United States Patent
Matossian-Rogers

(12)
(10) Patent No.: US 6,689,359 B1
(45) Date of Patent: Feb. 10, 2004

(54) LIGANDS, INCLUDING ANTIBODIES, SHOWING REACTIVITY AGAINST ENDOCRINE CELLS

(76) Inventor: Arpi Matossian-Rogers, 376 Finchley Road, London, NW3 7AJ (GB)

( * ) Notice: Subject to any disclaimer, the term of this patent is extended or adjusted under 35 U.S.C. 154(b) by 0 days.

(21) Appl. No.: 09/463,158
(22) PCT Filed: Jul. 20, 1998
(86) PCT No.: PCT/GB98/02151
§ 371 (c)(1),
(2), (4) Date: Jan. 20, 2000
(87) PCT Pub. No.: WO99/05175
PCT Pub. Date: Feb. 4, 1999

(30) Foreign Application Priority Data

Jul. 21, 1997 (GB) ............................................. 9715281
May 18, 1998 (GB) ............................................. 9810676

(51) Int. Cl.$^7$ ........................ C07K 16/42; C07K 16/28; C12P 21/08; A61K 39/395
(52) U.S. Cl. .............................. 424/131.1; 530/388.22; 530/388.7; 530/388.75; 530/389.6; 530/387.2; 530/391.1
(58) Field of Search ........................ 530/387.2, 388.22, 530/388.75, 388.7, 389.6, 391.1; 424/131.1

(56) References Cited

U.S. PATENT DOCUMENTS 5,589,328 A * 12/1996 Mahant
5,665,355 A * 9/1997 Primi
6,090,365 A * 7/2000 Kaminski et al.

FOREIGN PATENT DOCUMENTS

WO WO 91/09623 7/1991
WO WO 92/12996 8/1992

OTHER PUBLICATIONS

Ngo J.T, Marks J., Karplus M., Computational complexity, protein structure prediction, and the Levinthal paradox in The Protein Folding Problem, ch.14, pp. 435–508, Birkhauser, 1994.*

Male D, Immunology, An illustrated outline, 2nd edition, 1991.*

Acha–Orbea, H., "Anti–T–Cell Receptor $V_\beta$ Antibodies in Autoimmunity," *Ludwig Institute for Cancer Research*, XP–002086407, 1993, 193–202.

Celli, C.M., et al., "Origin and pathogenesis of antiphospholipid antibodies," *Brazilian J. Med. And Biol. Res.*, 1998, 31, 723–732.

David, C.S., et al., "A significant reduction in the incidence of collagen induced arthritis in mice treated with anti–TCR $V_\beta$ antibodies," XP–002086408, 1991, Supp. 15, Part E, 179 (Abstract).

De Giorgi, L., et al., "Murine hybridomas secreting monoclonal antibodies reacting with $^{Misa}$ antigens," *Exp. Clin. Immunogenet*, 1993, 10, 219–223.

Matossian–Rogers, A., et al., "Anti–T–cell receptor $V\beta6$ breaks tolerance in $^{Misa}$ antibodies," *Immunology*, 1993, 78, 122–126.

* cited by examiner

*Primary Examiner*—Christina Chan
*Assistant Examiner*—Maher Haddad
(74) *Attorney, Agent, or Firm*—Wenderoth, Lind & Ponack, L.L.P.

(57) ABSTRACT

The invention provides monoclonal and polyclonal antibodies recognising molecules on secretory cells of various tissue targets of autoimmune disease allowing a unifying method of preventing and treating autoimmune diseases and other conditions where hormonal dysregulation, hyperinsulinaemia and insulin resistance are involved. It also provides a method for detecting similar antibodies in human sera or other body fluids which can be used in the development of diagnostic kits. Treatment methods arising from this invention comprise the administration of preparations of the antibodies, their target molecules and vectors containing coding sequences of the antibodies and their target molecules.

13 Claims, 7 Drawing Sheets

FIG.6

```
GCAATTCCGG GATGAACAGG GCCCCATCCG CTGCAACACC ACAGTCTGCC TGGGCAAAAT
CGGCTCCTAC CTCAGTGCTA GCACCAGACA CAGGGTCCTT ACCTCTGCCT TCAGCCGAGC
CACTAGGGAC CCGTTTGCAC CGTCCCGGGT TGCGGGTGTC CTGGGCTTTG CTGCCACCCA
CAACCTCTAC TCAATGAACG ACTGTGCCCA GAAGATCCTG CCTGTGCTCT GCGGTCTCAC
TGTAGATCCT GAGAAATCCG TGCGAGACCA GGCCTTCAAG GCCATTCGGA GCTTCCTGTC
CAAATTGGAG TCTGTGTCGG AGGACCCGAC CCAGCTGGAG GAAGTGGAGA AGGATGTCCA
TGCAGCCTCC AGCCCTGGCA TGGGAGGAGC CCAGCTAGC CGCAGCTGAC TGGGCAGGCT GGGCCGTGAC
CGGGGTCTCC TCACTCACCT CCAAGCTGAT CCGTTCGCAC CCAACCACTG CCCCAACAGA
AACCAACATT CCCCAAAGAC CCACGCCTGA AGTTCCTGCC CCAGCCCCCA CCCCTGTTCC
TGCCACCCCT ACAACCTCAG GCCACTGGGA GACGCAGGAG GAGGACAAGG ACACAGCAGA
AGACAGCAGC ACTGCTGACA GATGGGACGA CGAAGACTGG GGCAGCCTGG AGCAGGAGGC
CGAGTCTGTG CTGGCCCAGC AGGACGACTG GAGCACCCGG GGCCAAGTGA GCCGTGCTAG
TCAGGTCAGC AACTCCGACC ACAAATCCTC CAAATCCCCA GAGTCCGACT TGGAGCAACT
GGGAAGCTTA AGGGTCCTTG GAACACGGCT GGCCAGCGAG TATAACTGGG GTTGCCCAGA
GTCCAGCGAC AAGGGCGACC CCTTCGCTAC CCTGTCTGCA CGTTCCAGCA CCCAGCCGAG
GCCAGACTCT TGGGGTGAGG ACAACTGGGA GGGCCTCGAG ACTGACAGTC GACAGGTCAA
GGCTGAGCTG GCCCGGAAGA AGCGCGAGGA GCGGCGGGCG GAGATGGAGG CCAAACGCGC
CGAGAGGAAG GTGGCCAAGG GCCCCATGAA GCTGGGAGCC CGGAAGCTGG ATGAACCGTG
GCGGTGGCCC TTCCCGGCTG CGGAGAGCCC CGGAGAGCCC TGTATTTATT GTACAAACCA
TGTGAGGCCG GCCGGCCCAG CCAGGCCATT CACGTGTACA TAATCAGAGC CACAATAAAT
TTTATTTCAC AAAAAAAAAA C
```

FIG. 7

```
QFRDEQGPIR CNTTVCLGKI GSYLSASTRH RVLTSAFSRA TRDPFAPSRV AGVLGFAATH
NLYSMNDCAQ KILPVLCGLT VDPEKSVRDQ AFKAIRSFLS KLESVSEDPT QLEEVEKDVH
AASSPGMGGA AASWAGWAVT GVSSLTSKLI RSHPTTAPTE TNIPQRPTPE VPAPAPTPVP
ATPTTSGHWE TQEEDKDTAE DSSTADRWDD EDWGSLEQEA ESVLAQQDDW STGGQVSRAS
QVSNSDHKSS KSPESDLEQL GSLRVLGTRL ASEYNWGCPE SSDKGDPFAT LSARSSTQPR
PDSWGEDNWE GLETDSRQVK AELARKKREE RRREMEAKRA ERKVAKGPMK LGARKLDEPW
RWPFPAAESP PHRCIYCTNH VRPAGPARPF TCT!SEPQ!I LFHKKKTGMA
```

LIGANDS, INCLUDING ANTIBODIES, SHOWING REACTIVITY AGAINST ENDOCRINE CELLS

This application is a U.S. national stage of International Application No. PCT/GB98/02151 filed Jul. 20. 1998.

FIELD OF INVENTION

This invention describes the development of unique autoantibodies which are the cause of several autoimmune and other diseases. It provides diagnostic and prophylactic uses for such antibodies in monoclonal and polyclonal form and also for the molecules recognised by the antibodies. More specifically, the invention provides for the use of these antibodies and the molecules they recognise as specific inhibitors of the development of autoantibodies with the same specificity in children and adults. These antibodies and target molecules are claimed to be of diagnostic, prophylactic and treatment use in a wide variety of autoimmune and other diseases. However, most of the background to the invention will focus on diabetes, not by way of limitation but by way of illustration or example.

The Spectrum of Human Autoimmune Diseases

Diseases associated with autoimmune phenomena can be classified within a spectrum ranging from conditions involving destructive lesions of a single organ or those in which organ or tissue damage is widely disseminated.

At the organ-specific end of the spectrum, the organs most commonly affected are the thyroid, adrenal glands, stomach and islets of Langerhans (which contain the insulin producing cells) in the pancreas, while at the non-organ specific pole, rheumatological or systemic (e.g. systemic lupus erythematosus) disorders predominate. Autoimmune diseases are, in rare cases, connected with fulminant viral infections which can also result in organ destruction. In autoimmunity, the damaging process is slow and sometimes it takes years before the disease becomes manifest. The following are organ-specific autoimmune diseases which result from autoimmune phenomena involving breakdown in immunological tolerance to self antigens.

Thyroid. Thyroid autoimmune disease involves a variety of clinical conditions which result in a common histopathological picture. There is diffuse infiltration of the gland by mononuclear lymphoid cells. The constituent diseases are primary myxoedema, Hashimoto's thyroiditis and Graves' disease. Progression from one to another is not uncommon. Primary myxoedema is the most common form of spontaneous hypothyroidism and is the last stage of the chronic inflammatory process. There is no goitre formation and the gland is almost completely atrophied.

Hashimoto's thyroiditis is also linked to hypothyroidism but is associated with goitre. In its various clinical forms, levels of thyroid hormone can either be compensated by increased levels of thyroid stimulating hormone (TSH) produced by the pituitary, or there can be clinical hypothyroidism in spite of raised TSH levels. In both autoimmune destructive conditions, women are affected five times more frequently than men.

The most common form of thyrotoxicosis is Graves' disease with or without goitre or exophthalmus. It is characterised by remissions and exacerbations. Despite that, the autoimmune process leads to hyperstimulation of the gland, due to the production of thyroid stimulating antibodies, final destruction of the thyroid often occurs. There is a female to male preponderance of 5:1.

In all thyroid autoimmune diseases, the demonstration of various autoantibodies to the gland confirms clinical diagnosis. Autoantibodies can be directed against thyroid cytoplasmic antigens, such as thyroglobulin, cell surface components, such as thyroid peroxidase, and thyrocyte surface expressed TSH receptors (i.e. Graves' disease).

Stomach. Autoimmune diseases of the stomach involve either the fundus or the antrum, leading to various degrees of inflammation affecting these two regions of the gland. In general, this process is named gastritis. In fundal gastritis, there is marked atrophy of the mucosa with consequent loss of intrinsic factor (IF) production leading to malabsorption of vitamin B12 and the subsequent development of pernicious anaemia. In these conditions, antibodies to IF and parietal cells are produced and are present in 90% of affected patients. Parietal cells are destroyed, but chief cells and mucus cells are also destroyed, despite the absence of circulating antibodies to the latter two cell types. There is a female to male preponderance of 3:1. Autoantibodies to gastrin-producing cells in the antrum have been demonstrated in some patients with antral gastritis. This type of gastritis is associated with gastric ulceration and in a proportion of patients, antibodies stimulating gastric cells have also been demonstrated.

Adrenals, Gonads and Placenta. Autoimmune disease of the adrenal (Addison's disease) is characterised by heavy mononuclear cell infiltration of the gland, adrenalitis, and the presence of autoantibodies to adrenal antigens. The symptoms are hyperpigmentation, weakness, fatigue, hypotension, gastro-intestinal symptoms and hypoglycaemia due to adrenal failure. Here again, the disease occurs mainly in women. By immunofluorescence the autoantibodies stain the three layers of the adrenal cortex, but a sub-type can also cross-react with analogous steroid-producing cells in the ovary, testis and placenta. When these latter specificities are present, they correlate with pre-clinical or clinically overt gonadal failure.

Pituitary. Lymphocytic hypophysitis is a rare autoimmune condition, resulting in hypopituitarism requiring hormone replacement therapy. There is a prevalence in females and the disease presents with a variety of other organ-specific autoimmune phenomena or associated disorders. Autoantibodies to prolactin-secreting cells can be detected, as well as other organ-specific antibodies in most cases.

Polyendocrine autoimmunity. Patients with organ-specific autoimmune disease may present with symptoms associated with failure of endocrine or other target organs (e.g. stomach). However, syndromes of multiple affected organs are not uncommon and autoantibodies to unaffected organs are also detectable in patients suffering with only one organ-specific disease. Thyroid and gastric autoimmunity are often seen in the same individual. Pernicious anaemia, resulting from fundal gastritis, is five times more frequent in patients with thyroid disorders and 30–50% of patients with pernicious anaemia also have a history of thyroid disease.

Associations also exist between adrenalitis and thyroiditis and adrenalitis and insulin dependent diabetes mellitus (IDDM). Often cases start with thyrotoxicosis and Addison's disease simultaneously and many patients with Addison's disease have at least one other autoimmune disease. Although hypophysitis and vitiligo (a condition which leads to patchy depigmentation of the skin, most likely due to autoimmune destruction of resident melanocytes) are rare, they often coexist with other overt organ specific conditions. The serological features, (i.e. the presence of circulating autoantibodies) which overlap among these autoimmune disorders is far more common than the co-existence of overt disease. For example, parietal cell antibodies are present in 50% of patients with thyroid disorders and 30% of patients with IDDM.

Current Knowledge Regarding the Pathology of IDDM

The current state of knowledge regarding the aetiology of IDDM (type I diabetes) focuses on the autoimmune destruction of islet $\beta$ cells in an environment of a variety of circulating autoantibodies, autoreactive T cells in the circulation and in pancreatic islets (insulitis) and a variety of cytokines. A pathogenic role for autoantibodies has thus far not been demonstrated but their presence has been shown to be of predictive value for the identification of preclinical diabetes particularly in first degree relatives of IDDM patients. Consequently the immunological attack resulting in IDDM is considered to be a T cell dependent $\beta$ cell destruction (Tisch and McDevitt; 1996). The evidence which lends support to this view is the presence of mononuclear cell infiltrates (insulitis) in the islets at disease onset (Gepts, 1965; Roep, and DeVries, 1992), the effect of immunosuppressive drugs in delaying disease onset (Bougneres et al., 1988), the destruction of pancreatic grafts in IDDM patients associated with insulitis (Sibley et al., 1985) and animal studies showing that splenic T-cells are able to transfer diabetes and both CD4 and CD8 T-cells are required (Bendelac el al., 1987). Cloned CD4 T cell lines with specificity for islet cell antigens have also been shown to be diabetogenic (Haskins and McDuffie, 1992). There is no evidence to date, however, that T cells cause the initial damage to islet $\beta$ cells or any indication as to what the target antigens might be.

Recently it has been demonstrated that autoreactivity of circulating T cells to islet cell antigens is not limited to IDDM patients but is also present in healthy, age matched controls even though to a lesser extent. It is therefore very likely that T-cell autoimmune phenomena are a consequence of $\beta$ cell dysfunction leading to $\beta$ cell damage.

Studies examining the cytokine profiles and Th1 and Th2 balances during disease progression in NOD mice have demonstrated that Th1 cells and Th1 type cytokines predominate at the onset of IDDM. A detailed study to examine the apparent correlation between the shift in cytokine levels and IDDM was carried out by Shimada et al. (1996). Splenocytes obtained from NOD and NOD-IA$^k$ and BALB/c control mice at various times during the disease process were separated to obtain CD45RB low (memory) CD4+ T cells; these were activated with anti-CD3 and the released cytokines assayed. A high IFN$\gamma$/IL4 ratio was found in NOD mice at, or just before, the onset of hyperglycaemia. The authors proposed that IDDM in the NOD mouse progresses as an inflammatory $\beta$ cell dysfunction without actual cell destruction until late in the disease process.

Dysfunction of $\beta$ cells indicated by elevated serum proinsulin levels relative to insulin or C-peptide has been noted at the clinical presentation of juvenile IDDM (Ludvigsson and Heding, 1982). Roder et al. (1994) studied 23 autoantibody positive siblings of IDDM patients, who were divided to 2 groups according to their first phase insulin response (FPIR) to intravenous glucose. Eleven siblings had diminished FPIRs and their fasting proinsulin/insulin or C-peptide ratios were 2–3 fold higher than the remainder of the siblings who had normal FPIRs. Nine of the 11 siblings with low FPIRs and high proinsulin/insulin or ratios became diabetic 1–28 months after testing, compared to none among the remainder of the siblings.

Dysfunction and eventual destruction of $\beta$ cells is characteristic of IDDM, however, both recent onset and long standing type 1 diabetics also have defective glucagon and epinephrine secretory responses and hepatic glucose production during hypoglycaemia (Kleinbaum el al., 1983). Carefully controlled studies using a hyperinsulinaemic hypoglycaemic clamp technique have demonstrated that glucagon levels rise during a 180 minute insulin infusion in normal but not in diabetic subjects (Barrou et al., 1994). Hepatic glucose production is also severely impaired in the latter group. This defect in counterregulation of hypoglycaemia is refractory to intensive medical management in many type 1 diabetics.

Although it is clear that glucagon secretion is impaired in long standing diabetics, not much is known about glucagon secretion in prediabetic individuals. Abnormalities in glucagon secretion have been demonstrated in animal models of diabetes. An investigation in prediabetic and overtly diabetic NOD mice revealed that in the prediabetic animals when fasting blood glucose and plasma insulin levels were normal, plasma glucagon levels were markedly elevated compared to control mice (Ohneda et al., 1984). Therefore an underlying metabolic disorder existed before the onset of diabetes.

Glucagon secreted from the pancreatic $\alpha$ cells is an important factor in maintaining normal control of euglycaemia by stimulating hepatic glucose production and also potentiating glucose induced insulin secretion. This was demonstrated by a drop in insulin secretion after immunoneutralisation of glucagon in fasted rats which was not accompanied by a drop in blood glucose (Brand et al., 1995).

Insulin release from FACS separated single $\beta$ cells is poor in response to nutrient challenge. This secretory defect can be fully restored by recombining the $\beta$ cells with separated $\alpha$ cells or by addition of (Bu)$_2$ cAMP or glucagon (Pipeleers et al., 1985). Glucagon is the major factor in elevating cAMP levels in $\beta$ cells (Rasmussen et al., 1990). Isolated $\beta$ cells exhibit lower levels of cAMP than $\beta$ cells in intact islets; increased or decreased c AMP levels in islets are paralleled by rising or falling secretory responses to glucose (Howell et al., 1973). The cAMP levels can be restored by reaggregation with non-$\beta$ islet cells or addition of glucagon (Schuit and Pipeleers, 1985). Compatible with a direct effect of glucagon on $\beta$ cells is the demonstration of glucagon receptors on $\beta$ cells (Van Schravendijk et al., 1985). Glucagon has also been shown to enhance the amplitude of pulsatile insulin release in response to glucose without affecting the periodicity of the secretory pulses (Marchetti et al., 1994).

Since it is well established that a rise in cytoplasmic Ca$^{2+}$ concentration is essential for insulin secretion (Prentki and Matschinsky, 1987), glucagon induced rises in cAMP levels have been proposed to act via increased Ca$^{2+}$ levels. Intricate experiments measuring Ca$^{2+}$ transients under the effect of photoreleased intracellular cAMP from a caged precursor demonstrated that the increase in Ca$^{2+}$ transients accounted for 10% of the total increase in exocytosis produced by cAMP (Ammala, et al., 1993). By similar methods Ammala et al., (1993) also demonstrated that cAMP initiates exocytosis at a Ca$^{2+}$ concentration which by itself is unable to promote secretion and also enhances exocytosis at higher Ca$^{2+}$ concentrations. Westerlund et al. (1997) also demonstrated that insulin secretion continued to be pulsatile under conditions when [Ca$^{2+}$]i remained stable. These experiments demonstrate that cAMP sets the threshold of sensitivity for the secretory action of Ca$^{2+}$ channel activation, whereby the role of glucagon (in increasing cAMP levels in $\beta$ cells) becomes of prime importance in controlling the amplitude of glucose induced fast insulin secretory pulses.

Glucagon secretion is also pulsatile, Storch et al., (1993) reported that the plasma concentration of glucagon in liver cirrhosis patients varied considerably in intervals of 4.1–6.5 minutes. In vitro perfused rat pancreata secreted both insulin and glucagon in pulses of 5.8 and 6.5 minutes respectively; reversing the direction of perfusion in rat and dog pancreata did not affect the periodicity of hormone secretion (Stagner and Samols, 1988). This negates the possibility that direct intra-islet hormonal interactions or a venous hormone sensitive receptor mechanism is responsible for the periodicity of secretion. Single mouse islets secrete insulin in response to glucose stimulation by both slow and fast oscillatory pulses (Bergsten et al., 1994). The mechanism therefore for pulsatile insulin secretion resides within individual islets; this is distinct from $[Ca^{2+}]i$ transients demonstrated by experiments involving activation of protein kinase C which increased the amplitude of oscillations without affecting their frequency or changes in $[Ca^{2+}]i$ (Deeney et al., 1996). These reports demonstrate that the pacemaker for pulsatility of insulin and glucagon secretion is located within the islets and is independent of extrinsic innervation and direct hormonal interaction. This has also been established in man by demonstration of both low and high frequency pulsatilities in successful pancreas transplants (Sonnenberg et al., 1992).

The Role of the Pacemaker in NIDDM

Beta-cell dysfunction is prominent in type 2 non-insulin-dependent diabetes (NIDDM) which is a disease also involving insulin resistance. The relative importance of these two components has been controversial. Early on in the disease there is a marked disruption in pulsatile insulin secretion with loss of the high frequency pulses and a reduction in amplitude of slow oscillations (Leahy, 1990; Guillausseau, 1994). The loss of pulsatile secretion may be an important potential contributor to insulin resistance. Various studies designed to identify predictors for the development of NIDDM have concluded that β cell dysfunction rather than insulin resistance is the major factor predisposing to NIDDM (Pimenta et al., 1995; Davis et al., 1995; Nijpels et al., 1996). Therefore the cause of NIDDM must be related to the event that induces the dysfunction. It is proposed herein that the dysfunction is consequent to the disruption of the pacemaker which maintains pulsatile secretion of both insulin and glucagon.

Parksen et al. (1995) have examined the contribution of pulsatile vs. basal insulin secretion in the overnight-fasted dog and have demonstrated that the majority of insulin (70%) was secreted as pulses. Disruption of this system would therefore have a major impact on total insulin secretion.

The natural history of β cell dysfunction preceding IDDM is more difficult to study because of the abrupt and destructive nature of the disease at diagnosis. O'Meara et al., (1995) were, however, able to study an individual over a 13-month period leading to the development of IDDM. When fasting glucose and glycosylated haemoglobin concentrations were still within normal range, insulin responses to intravenous glucose were reduced. The oscillatory pattern of secretion was preserved but the secretory responses were reduced.

DESCRIPTION OF THE INVENTION

The invention relates to a new concept regarding the cause of autoimmune diseases and specifically describes its application to types 1 and 2 diabetes as an illustration and not as a limitation. The present invention provides monoclonal or polyclonal antibodies or functionally equivalent ligands with reactivity against an anti-TCR Vβ antibody, for use as a pharmaceutical or as a diagnostic agent. These molecules may also exhibit reactivity against GPI-linked TCR Vβ chains, phospholipids, phospholipid glycans, single stranded DNA and/or double stranded DNA. The invention also provides the use of these antibodies in the manufacture of a medicament for the treatment of IDDM, NIDDM, or organ or non-organ specific autoimmune and related diseases. Preferably, a monoclonal antibody is used in accordance with the present invention.

With regard to diabetes, the invention implicates dysregulation of α cell function by newly identified autoantibodies with similar specificity as the said monoclonal antibodies as the major factor in the diabetogenic process. To substantiate this new concept, the invention demonstrates that the said monoclonal antibodies recognise a common epitope on a set of signalling molecules on α cells (which may function as the pacemaker in the islets) which are the targets of the said pathogenic autoantibodies.

The invention also provides for the detection of the said autoantibodies and furthermore embodies the use of these and the said MoAbs and the molecules recognised by these MoAbs in prophylactic and therapeutic interventions of autoimminue and related diseases including IDDM and NIDDM.

The monoclonal antibodies dysregulated insulin secretion from human islet cell cultures (see experimental section for details and Table 1). They were localised to α cells by simultaneously staining pancreatic sections with the said MoAbs (IgM) and also anti-glucagon MoAbs (IgG), detecting binding with fluoresceinated anti-mouse IgM and rhodaminated anti-mouse IgG respectively; the staining patterns of the antibodies were identical, demonstrating that both were staining the same glucagon producing α cells.

It is thought that the affect of the pathogenic autoantibodies on the α cell causes loss of both glucose counter-regulatory responsiveness and the fine-tuning of insulin secretion. The dysregulation of insulin secretion results either in β cell death leading to IDDM or continued survival of the β cell in the dysregulated state leading to NIDDM. These two outcomes are dependent upon the genetic susceptibility of the individual. In IDDM, T cell sensitisation is secondary to β cell damage and may accelerate the death of remaining β cells. However, the applicant does not wish to be bound by this theory.

The MoAbs which identified the α cell surface molecules were raised by immunising mice with anti-TCR Vβ monoclonal antibodies, as described below in the experimental section. Monoclonal antibodies produced by the resulting clones either recognised the anti-Vβ immunogen alone, or recognised the immunogen as well as phospatidyl inositol, phosphatidyl serine, cardiolipin (diacyl glycerol) and ds and ss DNA. These latter monoclonals also recognised human pancreatic α cells (FIG. 1), follicular cells of the thyroid (FIG. 2), cells of the adrenal medulla (FIG. 3), stomach and intestinal tract (FIG. 4), stomach, salivary glands, ovary, striated muscle, connective tissue, stated herein by way of example and not limitation.

As used herein, the term "functional equivalent" is intended to describe compounds that possess the desired binding site and includes any macromolecule or molecular entity that binds an anti-TCR Vβ antibody with a dissociation constant of $10^{-4}$M or less, preferably $10^{-7}$M or less, most preferably $10^{-9}$M or less, and that possesses an equivalent complementarity of shape to that possessed by the binding sites of the anti anti-TCR Vβ antibodies identified herein.

Current methods of generation of compounds with affinity for a molecule of interest have been until recently relatively primitive. The notion of combinatorial chemistry and the generation of combinatorial libraries has, however, developed at great speed and facilitated the rational design and improvement of molecules with desired properties. These techniques can be used to generate molecules possessing binding sites identical or similar to those of the antibodies identified herein.

Such compounds may be generated by rational design, using for example standard synthesis techniques in combination with molecular modelling and computer visualisation programs. Under these techniques, the "lead" compound with a similar framework to the antibody binding site is optimised by combining a diversity of scaffolds and component substituents.

Alternatively, or as one step in the structure-guided design of a molecular entity, combinatorial chemistry may be used to generate or refine the structure of compounds that mimic the relevant binding site by the production of congeneric combinatorial arrays around a framework scaffold. These steps might include standard peptide or organic molecule synthesis with a solid-phase split and recombine process or parallel combinatorial unit synthesis using either solid phase or solution techniques (see, for example Hogan, 1997 and the references cited therein).

Alternatively, or as a portion of a molecule according to this aspect of the present invention, functional equivalents may comprise fragments or variants of the identified antibodies or closely related proteins exhibiting significant sequence homology. By fragments is meant any portion of the entire protein sequence that retains the ability to bind to an anti-TCR Vβ antibody with a dissociation constant of $10^{-4}$M or less, preferably $10^{-7}$M or less, most preferably $10^{-9}$M or less. Accordingly, fragments containing single or multiple amino acid deletions from either terminus of the protein or from internal stretches of the primary amino acid sequence form one aspect of the present invention. Variants may include, for example, mutants containing amino acid substitutions, insertions or deletions from the wild type sequence of the antibody.

Biologically-active peptides with binding sites that mimic the antibodies described herein may be generated using phage libraries. Nucleic acids encoding amino acid residues identified as participants in the binding site, together with nucleic acid encoding the surrounding framework residues may be fused to give a polypeptide unit of between 10 and 1000 residues, preferably between 25 and 100 residues. By fusion of this nucleic acid fragment with that encoding a phage protein, for example pIII of the bacteriophage fd, the fusion molecule may be displayed on the surface of phage. Screening of the phage library with anti-TCR Vβ antibody will then identify those clones of interest. These clones can then be subjected to iterative rounds of mutagenesis and screening to improve the affinity of the generated molecules for their target.

The antibodies or functionally equivalent ligands according to the present invention may be of vertebrate or invertebrate origin. Preferably, the antibodies are derived from B cells immortalised by Epstein-Barr virus transformation or other methods using B cells obtained from healthy or diseased humans or animals.

The antibody or equivalent ligand may be isolated by passing body fluid from animals or humans down an antigen-conjugated column. The animals may have previously been immunised with antigen, may be diseased or may have been manipulated by drug or by diet so as to develop a disease.

According to a still further aspect of the invention, there is provided a peptide, oligopeptide, polypeptide or protein that is bound by the monoclonal or polyclonal antibody or equivalent ligand according to the first aspect of the invention, which is not an anti-TCR Vβ antibody, for use as a pharmaceutical or as a diagnostic agent. Of particular preference for use in this aspect of the present invention are proteins encoded by clones 1.1, 1.2, 1.3, 3.1, 4.1, 5.1, 5.2 or 5.3 as described below, fragments thereof and functional equivalents thereof. Such molecules may also be used in the manufacture of a medicament for the treatment of IDDM, NIDDM, or other organ or non-organ specific autoimmune and related diseases.

These molecules are recognised by the anti-anti-Vβ monoclonal antibodies and were identified by screening a human pancreas cDNA λgt11 library. Eight cDNA clones were purified and sequenced. Clones 1.1, 1.2 and 1.3 code for a secretogranin 1 like protein: clones 3.1, 4.1 and 5.1 coded for a 67 kd laminin receptor like protein; clone 5.2 coded for a new molecule that the inventor has named ESRP1 (endocrine secretion regulatory protein 1). Clone 5.3 codes for a human zymogen granule GP-2 protein-like protein.

The unifying characteristics of all these molecules is that they are linked to the cell membrane via a novel glycosyl phosphatidyl inositol (GPI) anchor. The regulation and expression of GPI-linked molecules on cell surfaces has been described (Low, 1989; Udenfriend and Kodukula, 1995). These acyl residues are sensitive to insulin action via insulin activated phospholipases (Chan et al. 1988). The cleavage products of these molecules are internalised by the α cells and are postulated herein to regulate glucagon secretion. The molecules require time to be resynthesised and reexpressed on the membrane which accounts for the periodicity of glucagon secretion and thus pulsatile secretion of both glucagon and insulin. This type of mechanism can account for the pacemaker in the islets. Antibodies which bind to the region on these molecules that undergo enzymatic cleavage can interfere with the action of the enzyme and thereby disrupt the regulation of glucagon and insulin secretion.

There are various mechanisms by which antibodies with similar specificity may arise physiologically in humans. Firstly, environmental agents such as infections or superantigens can induce clonal expansion of T cells and during this proliferative phase abnormally developed partial TCR complexes are retained intracellularly and degraded. T cells can apoptose under certain conditions and release degraded TCR products which can be immunogenic and trigger the cascade of anti-Vβ and anti-anti-Vβ network of antibody production. Secondly, it has been reported by Bell et al., (1994) that a signal peptide for a GPI anchor attachment is present in the TCRβ chain polypeptide sequence and that TCRβ chains lacking the cytoplasmic tail sequence are expressed on a mature T cell hybridoma line as a GPI-anchored monomeric polypeptide in the absence of TCRα. GPI-linked TCRβ chains have been detected in TCRβ transgenic mice but not in normal mice: therefore the abnormal expression of such Vβ chains can induce a cascade of network responses resulting in antibodies of similar specificity to anti-anti-Vβ reagents. Such antibodies were detected in human sera in another embodiment of this invention (see Table 2 in experimental section).

The cDNA clones mentioned above and the proteins that they encode are described in further detail below:

Clones 1.1, 1.2, 1.3. These three clones 1500 bp, 1400 bp and 900 bp respectively code for a Secretogranin 1 (Sg1)

like molecule. Secretogranin 1 is a 657 amino acid long polypeptide of 76 kd and is preceded by a cleaved N-terminal signal peptide of 20 residues (Benedum et al., 1987). It has a disulfide bonded loop structure and is a secretory protein sorted to secretory granules of endocrine cells and neurones. It was demonstrated by Pimplikar and Huttner, (1992) that in the neuroendocrine cell line PC12, a fraction of exocytosed Sg1 was not released but remained associated with the plasma membrane. The surface Sg1 (approximately 10% of the total cellular protein) was internalised and degraded indicating possible signalling properties. This polypeptide has the characteristics of a caveolar protein (Chang el al., 1994). The promoter region of the mouse Sg1 gene contains a cAMP-responsive element (Pohl et al., 1990). Secretogranins are a family of acidic proteins. Because they are not found in exocrine cells they have been used as immunohistochemical diagnostic markers for endocrine tumours. In addition Sg1 is a heparin-binding adhesive protein and has been shown to mediate substratum adhesion (Chen el al., 1992). It is of interest that in the rodent Sg1 mRNA accumululation begins around embryonic days 13–14 and peaks by postnatal day 20 (Foss-Peters et al., 1989).

Clones 3.1, 4.1, 5.1. Three other clones 3.1(900 bp), 4.1(900 bp) and 5.1(1000 bp) code for a 67 kd laminin receptor like protein. Laminin is a major component of basement membranes which plays an important role in a variety of cell functions such as adhesion, tissue remodelling, wound healing, inflammation, tumour cell metastasis etc. Interaction of the extracellular matrix (ECM) with cells in contact with it is via distinct cell surface receptors such as the 67 kd laminin receptor. This laminin binding protein also binds elastin, collagen type IV and is a galactolectin which enables its purification on glycoconjugate affinity columns containing β galactosugars. Beta galactose sugars such as galactose and lactose can elute this protein from elastin or laminin affinity columns (Hinek, 1994). The binding of galactosugars to the lectin site on the molecule not only has the effect of displacing the ECM ligands from their binding site but also dissociates the 67 kd protein from the cell membrane (Hinek et al., 1992). It has also been demonstrated that there is a relationship between deficiency of this protein on smooth muscle cells from ductus arteriosus, their detachment from elastin and their capability of migration.

The surface expression of this protein is likely to be under translational regulation. Transfected cells which expressed high levels of mRNA did not always express correspondingly high levels of the protein on their surface. (Landowski, et al., 1995). Microspectrofluorometry and videomicroscopy experiments have demonstrated that the binding of elastin or the active peptide VGVAPG (SEQ ID NO:7) to aortic smooth muscle results in a transient increase in free intracellular $Ca^{2+}$. This suggests that cell surface laminin or elastin binding protein acts as a true receptor mediating intracellular signalling (Hinek, 1994).

There is still controversy regarding the mode of attachment of this protein to the cell membrane as analysis of the predicted amino acid sequence has not revealed any hydrophobic domains characteristic of a transmembrane region. Methyl esterification of the purified protein followed by gas chromatography and mass spectrometry has indicated that the protein is acylated by covalently bound fatty acids, palmitate, stearate and oleate but the linkage chemistry has not been definitively identified (Landowski et al., 1995). Acylation of this protein confers on it a further set of properties apart from those dependent upon laminin binding. Lipid modifications have been shown to affect protein-protein interactions and acyl modifying groups may also generate second messengers in signal transduction.

Clone 5.2. The polypeptide encoded by this approximately 1200 bp cDNA clone has no significant similarity to a functionally characterised protein. It is therefore not possible to obtain any functional comparisons with any known proteins. It is thought, however, that this protein shares an epitope with the proteins identified by the monoclonal anti-anti-Vβ used in screening the pancreas library and therefore shares similar functional properties. This protein will henceforth be called endocrine secretion regulatory protein 1 (ESRP1).

According to a further embodiment of the invention, there is provided the protein ESRP1, fragments thereof and functional equivalents. The sequence of the protein is provided in FIG. 7 below. The sequence of the encoding nucleic acid forms a further aspect of this embodiment of the invention and is provided in FIG. 6 below.

According to a further aspect of the present invention there is provided the ESRP1 protein for use in therapy or diagnosis.

An ESRP1 protein or functional equivalent according to the present invention may be derived from any organism possessing a protein in the same family as the compounds identified herein. By protein family is meant a group of polypeptides that share a common function and exhibit common sequence homology between motifs present in the polypeptide sequences.

Preferably, the protein, protein fragment or functional equivalent is derived from a mammal, preferably the human.

According to a still further aspect of this embodiment of the present invention there is provided the use of the ESRP1 protein, fragments thereof and functional equivalents in the manufacture of a medicament for the treatment of IDDM, NIDDM, organ or non-organ specific autoimmune disease, cardiovascular disease, cancer cachexia and cancer and any other diseases where anti-phospholipid antibodies and/or hyperinsulinaemia and insulin resistance are present.

As used throughout this specification, the term "organ or non-organ specific autoimmune disease" is meant to include IDDM, NIDDM, autoimmune diseases of the thyroid, adrenal gland, gonads, stomach and pituitary, systemic lupus erythematosus, systemic sclerosis and Sjogren's syndrome. "Cardiovascular disease" is meant to include coronary and carotid artery disease, macro and micro-vascular angina, peripheral vascular disease, atherosclerosis and hypertension. "Cancer" is meant to include breast, colorectal, gastric, endometrial, prostate, head and neck, lung sarcomas, "Other suitable disease" is meant to include polycystic ovary syndrome, obesity, Cushing's syndrome and metabolic syndrome X. These diseases are given as examples and not as limitations.

Clone 5.3. This approximately 2000 bp cDNA clone codes for protein that is very similar to the exocrine human zymogen granule membrane GP-2 protein. However, clone 5.3 has several nucleic acid and consequently amino acid differences and is located in the endocrine pancreas.

Since the antibody reactive with this cDNA clone stains the endocrine pancreas, the protein it codes for is thought to be the endocrine counterpart of the exocrine GP-2 protein. This does not, however, confer upon this protein the same function in the endocrine cells as it has in the exocrine tissue. Rat GP-2 expressed in cell lines of endocrine or exocrine origin by cDNA transfection, was shown to be targeted to secretory granules in the exocrine cells but not in the endocrine (Hoops et al., 1993).

The major protein in isolated zymogen granule membranes of the exocrine pancreas is GP-2 which accounts for up to 40% of the total protein (Ronzio et al., 1978). Both the human and rat proteins are attached to the granule membrane via a glycosyl phosphatidyl inositol (GPI) linkage and can be released from the membrane by phosphatidyl inositol-specific phospholipase C (PI-PLC). The high content of GP-2 in zymogen granule membranes has led to the hypothesis that this protein is important in granule formation. It has, however, been reported that GP-2 mRNA is absent from the embryonic rat pancreas and GP-2 is expressed only after birth during the period of weaning. Since the embryonic rat pancreas contains plenty of granules it can be inferred that GP-2 is not essential for granule formation (Dittie and Kern, 1992). These observations have been confirmed in studies of the pig pancreas where the GP-2 protein and mRNA are also absent in the foetus and only start being produced 21 days after birth. Foetal granules are therefore completely devoid of GP-2 protein (Laine el al., 1996). The emergence of antigens at the time of weaning could explain the concomitant development of insulitis at this time in experimental animal models of diabetes.

The precise functional role/s of GP-2 protein are not known but since the protein exists both in soluble form (40%) and membrane bound (60%) in the zymogen granules it must have both intracellular and extracellular functions. Since the GP-2 protein is expressed after birth in rodents and pigs, tolerance to this molecule must be peripherally induced rather than intrathymically during embryonic development. Pulendran et al. (1995) and Shokat and Goodnow (1995) have demonstrated that germinal centre B cells become apoptotic upon encountering soluble antigen. Therefore soluble GP-2 may have the role of inducing tolerance by binding to the immunoglobulin receptor of GP-2 reactive germinal centre B cells and triggering apoptosis.

The membrane bound form of GP-2 can be released from the membrane by proteases and phospholipases; the presence of inositol 1,2-(cyclic) monophosphate on secreted hydrophilic GP-2 has been demonstrated confirming the action of a phospholipase C in the cleaving of GP-2 from the membrane (Paul el al., 1991). The lipid products such as 1,2-diacylglycerol and phosphatidic acid or inositol glycan derived from lipid anchors of cell surface proteins by phospholipases, proteases or hydrolases may be internalised and participate in second messenger pathways. GPI-linked proteins may also be directly involved in signal transduction via crosslinking of their $NH_2$ terminal domains. The signal transduction is via the src family protein tyrosine kinases p56 lck and p59 fyn and involves the GPI anchor (Shenoy-Scaria et al., 1992). GP-2 protein has also been shown to have enzymatic properties and has been identified as a nucleoside phosphatase with di- and tri-phosphatase activities within the zymogen granule membrane of the pig. This implies that it is involved in energy-requiring processes in the cytosol (Soriani and Freiburghaus, 1996).

The GP-2 protein has 53% identity and 85% similarity to the human Uromodulin/Tamm-Horsfall (THP) protein over a 450 amino acid stretch at the C-terminal region. THP is also GPI-linked and both proteins belong to a family of proteins including the sperm receptors Zp2 and Zp3 and β glycan (TGF-β type III receptor) and are characterised by a 260 residue domain common to these apparently diverse proteins (Bork and Sander, 1992). The newly identified α cell protein encoded by the 2000 bp cDNA clone must also belong to this family of proteins and must have a significant function in the control of the secretory process of α cells.

For many applications, an antibody or equivalent ligand according to the first aspect of the present invention or peptide, oligopeptide, polypeptide or protein recognised by such an antibody may be fused to an effector or reporter molecule such as a label, toxin or bioactive molecule. According to a further aspect of the invention there is provided an antibody or equivalent ligand according to the first aspect of the invention or a peptide, oligopeptide, polypeptide or protein recognised by such an antibody that is chemically-modified, bound to a biological or synthetic substance, or conjugated to an enzyme, an indicator compound, a drug, a toxin or a radioactive label, for use as a pharmaceutical or as a diagnostic agent.

Suitable labels will be well known to those of skill in the art. For example, such labels may comprise an additional protein or polypeptide fused to an antibody, fragment thereof, or equivalent ligand at its amino- or carboxy-terminus or added internally. The purpose of the additional polypeptide may be to aid detection, expression, separation or purification of the antibody, fragment thereof, or equivalent ligand or may be to imbue additional properties to the antibody, fragment thereof, or equivalent ligand as desired.

Particularly suitable candidates for fusion will be reporter molecules such as luciferase, green fluorescent protein, or horse radish peroxidase. Labels of choice may be radiolabels or molecules that are detectable spectroscopically, for example fluorescent or phosphorescent chemical groups. Linker molecules such as streptavidin or biotin may also be used. Additionally, other peptides or polypeptides may be used as fusion candidates. Suitable peptides may be, for example, β-galactosidase, glutathione-S-transferase, luciferase, polyhistidine tags, secretion signal peptides, the Fc region of an antibody, the FLAG peptide, cellulose binding domains, calmodulin and the maltose binding protein.

These fusion molecules may be fused chemically, using methods such as chemical cross-linking. Suitable methods will be well known to those of skill in the art and may comprise for example, cross-linking of the thiol groups of cysteine residues or cross-linking using formaldehydes. Chemical cross-linking will in most instances be used to fuse non-protein compounds, such as cyclic peptides and labels.

When it is desired to fuse two or more protein molecules, the method of choice will often be to fuse the molecules genetically. In order to generate a recombinant fusion protein, the genes or gene portions that encode the proteins or protein fragments of interest are engineered so as to form one contiguous gene arranged so that the codons of the two gene sequences are transcribed in frame.

The compounds of the present invention may also be bound to a support that can be used to remove, isolate or extract anti-anti-TCR Vβ antibodies from body tissues. The support may comprise any suitably inert material and includes gels, magnetic and other beads, microspheres, binding columns and resins.

Protein or peptide compounds according to the invention will preferably be expressed in recombinant form by expression of the encoding DNA in an expression, vector in a host cell. Such expression methods are well known to those of skill in the art and many are described in detail in *DNA cloning: a practical approach, Volume II: Expression systems*, edited by D. M. Glover (IRL Press, 1995) or in *DNA cloning: a practical approach, Volume IV: Mammalian systems*, edited by D. M. Glover (IRL Press, 1995). Protein compounds may also be prepared using the known techniques of genetic engineering such as site-directed or random mutagenesis as described, for example, in *Molecular*

*Cloning: a Laboratory Manual*: 2nd edition, (Sambrook el al., 1989, Cold Spring Harbor Laboratory Press) or in *Protein Engineering: A practical approach* (edited by A. R. Rees et al., IRL Press 1993).

Suitable expression vectors can be chosen for the host of choice. The vector may contain a recombinant DNA molecule encoding compounds of the present invention operatively linked to an expression control sequence, or a recombinant DNA cloning vehicle or vector containing such a recombinant DNA molecule under the control of a promoter recognised by the host transcription machinery.

Suitable hosts include commonly used prokaryotic species, such as *E. coli*, or eukaryotic yeasts that can be made to express high levels of recombinant proteins and that can easily be grown in large quantities. Mammalian cell lines grown in vitro are also suitable, particularly when using virus-driven expression systems such as the baculovirus expression system which involves the use of insect cells as hosts. Compounds may also be expressed in vivo, for example in insect larvae or in mammalian tissues.

According to a further aspect of the present invention there is provided a pharmaceutical composition comprising a monoclonal or polyclonal antibody or functionally equivalent ligand with reactivity against an anti-TCR Vβ antibody or a peptide, oligopeptide, polypeptide or protein recognised by such antibodies (which is not an anti-TCR Vβ antibody), in conjunction with a pharmaceutically-acceptable excipient. Suitable excipients will be well known to those of skill in the art and may, for example, comprise a phosphate-buffered saline (0.001M phosphate salts. 0.138M NaCl, 0.0027M KCl, pH7.4). Pharmaceutical compositions may also contain additional preservatives to ensure a long shelf life in storage.

The monoclonal or polyclonal antibody or functionally equivalent ligand with reactivity against an anti-TCR Vβ antibody or peptide, oligopeptide, polypeptide or protein recognised by such an antibody may constitute the sole active component of the composition or can form part of a therapeutic package for topical (such as a component of a cream), oral or parenteral administration.

According to a further aspect of the present invention there is provided the use of an antibody or equivalent ligand with reactivity against an anti-TCR Vβ antibody in the manufacture of a medicament for the treatment of IDDM, NIDDM, or other organ or non-organ specific autoimmune disease, cardiovascular disease, cancer cachexia and cancer or any other diseases where anti-phospholipid antibodies and/or hyperinsulinaemia and insulin resistance are present.

According to a still further aspect of the present invention there is provided a method of treatment of IDDM, NIDDM, or other organ or non-organ specific autoimmune disease, cardiovascular disease, cancer cachexia and cancer or any other diseases where anti-phospholipid antibodies and/or hyperinsulinaemia and insulin resistance are present.

According to a still further aspect of the present invention there is provided the use of a peptide, oligopeptide, polypeptide or protein that is bound by a monoclonal or polyclonal antibody or equivalent ligand with reactivity against an anti-TCR Vβ antibody, which is not an anti-TCR Vβ antibody, in the manufacture of a medicament for the treatment of IDDM, NIDDM, or other organ or non-organ specific autoimmune disease, cardiovascular disease, cancer cachexia and cancer or any other diseases where anti-phospholipid antibodies and/or hyperinsulinaemia and insulin resistance are present.

According to a further embodiment of the invention, there is provided a method for the detection of a naturally-occurring autoantibody, comprising contacting a blood, plasma or serum sample or other body fluid with a monoclonal or polyclonal antibody or equivalent ligand according to the first aspect of the invention and with target molecules and assessing the amount of said naturally-occurring autoantibody that binds specifically to the target molecules. The monoclonal or polyclonal antibody or equivalent ligand may be labelled, for example with an enzyme, so that the labelled antibody or equivalent ligand competes with the autoantibodies for the target molecules to form complexes. The amount of label bound in said complexes is thereby inversely proportional to the concentration of autoantibodies present in said sample. If labelled with an enzyme, the formation of the complexes will inhibit or inactivate the activity of the enzyme so that the degree of inhibition or activation is inversely proportional to the concentration of autoantibodies that are present in the sample.

In one aspect of this embodiment of the invention, the target molecule, which may be for example an anti-TCR Vβ polyclonal or monoclonal immunoglobulin molecule or any part thereof that identifies at least one epitope on T cell receptor Vβ chains in humans or any other animal species, is bound to an enzyme linked to a substrate such that binding of antibody to the target molecules activates the enzyme and causes a colour change that is measurable spectrophotometrically. The target molecules may be bound to an enzyme that is linked to the substrate and may be present on a dipstick which can be contacted with said sample.

The invention also comprises the use of an antibody or equivalent ligand with reactivity against an anti-TCR Vβ antibody or a peptide, oligopeptide, polypeptide or protein that is bound by a monoclonal or polyclonal antibody or equivalent ligand with reactivity against an anti-TCR Vβ antibody (for example ESRP1) as a component in a kit for the detection or quantification of levels of naturally-occurring autoantibodies in a patient. Such a kit will resemble a radioimmunoassay or ELISA kit and would additionally comprise detection means that allows the accurate quantification of the compound of interest. Such methods will be apparent to those of skill in the art.

The antibody or equivalent ligand or peptide, oligopeptide, polypeptide or protein that is bound by the monoclonal or polyclonal antibody or equivalent ligand may be bound to magnetic beads, agarose beads or may be fixed to the bottom of a multiwell plate. This will allow the removal of the unbound compounds from the sample after incubation. Alternatively the protein may be bound to SPA (Scintillation Proximity Assay) beads, in which case there is no need to remove unbound ligand. Using a set of unlabelled standards, the results obtained with these standards can be compared with the results obtained with the sample to be measured.

The antibody or equivalent ligand with reactivity against an anti-TCR Vβ antibody or peptide, oligopeptide, polypeptide or protein that is bound by a monoclonal or polyclonal antibody or equivalent ligand with reactivity against an anti-TCR Vβ antibody can also be used for the detection of naturally-occurring autoantibodies in tissue from a patient. Any technique common to the art may be used in such a detection method and may comprise the use of blotting techniques (Towbin et al., 1979), binding columns, gel retardation, chromatography, or any of the other suitable methods that are widely used in the art.

The invention also provides a cDNA, RNA or genomic DNA sequence comprising a sequence encoding an antibody or equivalent ligand according to the first aspect of the invention or encoding a peptide, oligopeptide, polypeptide or protein according to the second aspect of the invention, for use as a pharmaceutical or as a diagnostic agent.

With regard to the protein ESRP1, the preferred nucleic acid molecule comprises a nucleotide fragment identical to or complementary to any portion of the nucleotide sequence shown in the accompanying FIG. 6 or a sequence which is degenerate or substantially homologous therewith, or which hybridises with the said sequence. By 'substantially homologous' is meant sequences displaying at least 50% sequence homology, preferably 60% sequence homology. 'Hybridising sequences' included within the scope of the invention are those binding under standard non-stringent conditions (6×SSC/50% formamide at room temperature) and washed under conditions of low stringency (2×SSC, room temperature, or 2×SSC, 42° C.) or preferably under standard conditions of higher stringency, e.g. 0.1×SSC, 65° C. (where SSC=0.15M NaCl, 0.015M sodium citrate, pH 7.2).

A nucleic acid sequence according to the invention may be single- or double-stranded DNA, cDNA or RNA. Preferably, the nucleic acid sequence comprises DNA.

The invention also includes cloning and expression vectors containing the DNA sequences of the invention. Such expression vectors will incorporate the appropriate transcriptional and translational control sequences, for example enhancer elements, promoter-operator regions, termination stop sequences, mRNA stability sequences, start and stop codons or ribosomal binding sites, linked in frame with the nucleic acid molecules of the invention.

Additionally, in the absence of a naturally-effective signal peptide in the protein sequence, it may be convenient to cause the recombinant protein to be secreted from certain hosts. Accordingly, further components of such vectors may include nucleic acid sequences encoding secretion signalling and processing sequences.

Vectors according to the invention include plasmids and viruses (including both bacteriophage and eukaryotic viruses). Many such vectors and expression systems are well known and documented in the art. Particularly suitable viral vectors include baculovirus-, adenovirus- and vaccinia virus-based vectors.

The expression of heterologous polypeptides and polypeptide fragments in prokaryotic cells such as *E. coli* is well established in the art; see for example *Molecular Cloning: a Laboratory Manual*: 2nd edition, Sambrook et al., 1989, Cold Spring Harbor Laboratory Press or *DNA cloning: a practical approach, Volume II: Expression systems*, edited by D. M. Glover (IRL Press, 1995). Expression in eukaryotic cells in culture is also an option available to those skilled in the art for the production of a heterologous proteins; see for example O'Reilly et al., (1994) *Baculovirus expression vectors—a laboratory manual* (Oxford University Press) or *DNA cloning: a practical approach, Volume IV: Mammalian systems*, edited by D. M. Glover (IRL Press, 1995).

Suitable vectors can be chosen or constructed for expression of peptides or proteins suitable for use in accordance with the present invention, containing the appropriate regulatory sequences, including promoter sequences, terminator sequences, polyadenylation sequences, enhancer sequences, marker genes and other sequences as appropriate. Vectors may be plasmids, viral e.g. bacteriophage, or phagemid, as appropriate. For further details see *Molecular Cloning: a Laboratory Manual*. Many known techniques and protocols for manipulation of nucleic acid, for example, in the preparation of nucleic acid constructs, mutagenesis, sequencing, introduction of DNA into cells and gene expression, and analysis of proteins, are described in detail in *Short Protocols in Molecular Biology*, Second Edition, Ausubel et al, eds., (John Wiley & Sons, 1992) or *Protein Engineering: A practical approach* (edited by A. R. Rees et al., IRL Press 1993). For example, in eukaryotic cells, the vectors of choice are virus-based.

A further aspect of the present invention provides a host cell containing an antibody or equivalent ligand according to the first aspect of the invention or encoding a peptide, oligopeptide, polypeptide or protein according to the second aspect of the invention. A still further aspect provides a method comprising introducing such nucleic acid into a host cell or organism. Introduction of nucleic acid may employ any available technique. In eukaryotic cells, suitable techniques may include calcium phosphate transfection, DEAE-Dextran, electroporation, liposome-mediated transfection or transduction using retrovirus or other viruses, such as vaccinia or, for insect cells, baculovirus. In bacterial cells, suitable techniques may include calcium chloride transformation, electroporation or transfection using bacteriophage.

Introduction of the nucleic acid may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences that promote recombination with the genome, in accordance with standard techniques.

Transgenic animals transformed so as to express or over-express in the germ line one or more compounds as described herein form a still further aspect of the invention, along with methods for their production. Many techniques now exist to introduce transgenes into the embryo or germ line of an organism, such as for example, illustrated in Watson el al., (1994) Recombinant DNA (2nd edition), Scientific American Books.

Therapeutic Implications of the Invention and Application to Unanswered Questions in Diabetes The following are given by way of example and not by way of limitation.

Impaired Glucose Counterregulation

A major problem in the management of IDDM patients is the occurrence of hypoglycaemia which may be partially iatrogenic due to intensive insulin treatment leading to hypoglycaemia unawareness, but is mainly due to compromised glucose counterregulation. Defective glucose counterregualtion is the result of the combined deficiencies of the glucagon and epinephrine responses to falling glucose levels. It has been demonstrated that scrupulous avoidance of hypoglycaemia can reverse hypoglycaemia unawareness but not defective counterregulation (Cryer, 1995).

Not only longstanding but also newly diagnosed IDDM patients have impaired counterregulation. A comparison of counterregulatory responses in twenty children with new onset IDDM (5–6 days) and 47 children with long standing onset IDDM, revealed that glucagon responses to hypoglycaemia in both groups were lower than in control subjects. Epinephrine responses were also reduced in new IDDM patients compared to controls (Hoffman el al., 1994).

It is proposed herein that the reason for these counterregulatory defects is the persistence of auto-anti-anti-Vβ antibodies in IDDM patients causing downregulation of the signalling molecules described above and abrogating the response of alpha cells and adrenal medullary cells to falling glucose levels. This is in keeping with the observation of loss of anti-anti-Vβ staining of pancreatic sections from a newly diagnosed diabetic patient who died accidentally (see experimental section p39). It is also analogous to the findings of Brett el al. (1996) that treatment of rheumatoid arthritis patients with Campath-1H which is against the GPI-linked CD52 protein, resulted in disappearance of CD52 and other GPI-linked proteins on both T cells and B cells of some of the patients treated. The CD52-negative B cells disappeared from the circulation within 3 months; however, the CD52-negative T cells persisted for at least 20 months. Therefore preventing the perpetuation of these antibodies in IDDM patients should ameliorate counterregulatory defects preventing hypoglycaemia. Blocking their development from birth should prevent IDDM in susceptible individuals, NIDDM should be cured entirely. This will be accomplished by a method analogous to the administration of anti-D immunoglobulin (anti-D Ig) to Rh-negative mothers carrying Rh-positive foetuses (Davey, 1979). Possible mechanisms which are involved in the blocking of antibody production in this type of therapy are discussed by Heyman (1990). As a further measure, immunising individuals with the pathogenic antibodies should generate protective anti-idiotypic antibodies which can then complex with the pathogenic antibodies when they arise.

Diabetic Nephropathy

Renal involvement in type I diabetes is characterised by epithelial and basement membrane hypertrophy of the glomeruli and tubules and accumulation of extracellular matrix components in the glomerular mesangium (Lane el al., 1990). Progression of the disease leads to obliteration of the glomerular capillary lumen, proteinuria and loss of filtration. Hyperglycaemia and production of TGF-β (transforming growth factor) have been implicated in diabetic nephropathy. High glucose concentrations increase TGF-β mRNA and protein in cultures of mesangial and proximal tubular cells; the TGF-β indirectly mediates the effects of glucose on cell growth and collagen synthesis. Administration of antiserum against TGF-β has been shown to suppress experimental glomerulonephritis (Border, 1990).

It is likely that hyperglycaemia induces TGF-β expression early in diabetes; this is supported by the fact that both in human diabetes and in the BB and NOD models, increased renal expression of TGF-β has been demonstrated within a few days after the onset of hyperglycaemia and renal hypertrophy (Yamamoto el al., 1993; Sharma and Ziyadeh, 1994).

The binding of TGF-β to its receptor is assisted by a membrane anchored proteoglycan (β glycan) that presents TGF-β to the type II signalling receptor, a transmembrane serine/threonine kinase (Lopez-Castillas et al., 1994). Beta-glycan has an extracellular region which is shed by cells and can bind TGF-β but cannot present it to the signalling receptor and consequently acts as a potent inhibitor of its action. Betaglycan belongs to a family of proteins which includes uromodulin and the pancreatic secretory granule membrane GP-2. The role of the uromodulin related region in TGF-β binding has been demonstrated (Fukushima et al., 1993).

The α cell molecule related to GP-2 (product of clone 5.3) which exists in soluble and membrane bound form may be one of the proteins involved in the inhibition of TGF-β action. The down regulation of these molecules due to prolonged action of the pathogenic antibodies may result in the abrogation of TGF-β inhibition, thus promoting its trophic properties in the kidney. Administration of soluble peptides of the molecules recognised by the pathogenic antibodies would have the dual role of inhibiting TGF-β and suppressing antibody production.

Pancreas Transplantation

Transplantation is increasingly being performed to treat type 1 diabetics prone to severe hypoglycaemic episodes. This has the dual role of establishing insulin independence and partially restoring normoglycaemia. If this procedure, however, is carried out without counteracting the underlying diabetogenic conditions, the glucose counterregulatory problems will reemerge with each successive episode of pathogenic antibody development.

In a recent study of 13 successful pancreas transplant patients using a stepped hypoglycaemic clamp technique, it was demonstrated that glucagon responses to hypoglycaemia were restored. However, both fasting and stimulated glucagon levels were significantly greater in the pancreas transplant recipients compared to normal controls or kidney transplant recipients. Furthermore, C-peptide levels were also raised compared to all other groups (Kendall et al., 1997). The authors did not comment on these observations which are reminiscent of a prediabetic condition. They reported, however that epinephrine responses to hypoglycaemia were improved in the pancreas transplant recipients but were significantly lower than in healthy control subjects or non-diabetic kidney transplant recipients. It is clear from these observations that transplantation of a healthy pancreas into a diabetic patient sets the clock back to the prediabetic state in terms of both the α cells and the adrenal response. A potential diabetic pancreas transplant patient must be treated to prevent further episodes of rises in pathogenic antibody titres prior to transplantation to ensure complete success of the procedure.

Autonomic Neuropathy

Diabetes of long standing may be complicated by autonomic neuropathy which is irreversible and distinct from hypoglycaemia unawareness (Cryer, 1994; Dagogo-Jack et al., 1993). The elimination of hypoglycaemia by means of pancreas transplantation in the study of Kendall et al., (1997) improved both the epinephrine response and hypoglycaemic symptom recognition despite the persistence of cardiac autonomic dysfunction. A norepinephrine response, however, which was absent in the long-standing diabetic patients was not restored by pancreas transplantation. Although the reactivity of the diabetogenic monoclonal antibodies against the neuronal cell bodies in the autonomic ganglia has not yet been tested, it is anticipated that the antigens they recognise will also be present on these cell bodies. The expression of unique sets of GPI-linked proteins on different primary neurones has been demonstrated. Some of these have been shown to correspond to different ensheathment characteristics (Rosen et al., 1992). Such molecules will have, similar signalling properties and may be affected similarly to those on α cells and adrenal medullary cells.

The GPI-linked membrane protein, ciliary neurotrophic factor receptor(CNTF) has already been implicated in some forms of peripheral diabetic neuropathy. In hyperglycaemia induced by galactose feeding or streptozotocin treatment of experimental animals, the levels of CNTF-like activity in sciatic nerve were reduced after 1–2 months of hyperglycaemia. This has been associated with reduction of CNTF protein but not mRNA. Deficits of CNTF resulting from Schwann cell injury may contribute to certain functional and structural abnormalities in experimental diabetic neuropathy. Some of these abnormalities are due to aldose reductase (AR) metabolism of hexoses and can be prevented by AR inhibitors. However, CNTF deficiency was only partially restored by these inhibitors indicating that factors other than polyol accumulation due to AR activity are involved in reduction of CNTF expression (Mizisin et al., 1997). This demonstrates that GPI-linked molecules may play a significant role in peripheral diabetic neuropathy as well as autonomic neuropathy.

Therapeutic Implications of the Invention and Application to Unanswered Questions in SLE and the Primary Anti-phospholipid Syndrome The following are given by way of example and not by way of limitation.

Antibodies with specificity against anionic phospholipids such as cardiolipin have been associated with thrombosis, recurrent foetal loss and thrombocytopenia (Harris el al., 1983; Cowchock el al., 1986; Harris et al., 1986). Similar claims have been made for systemic lupus erythematosus (SLE) associated antibodies called lupus anticoagulant which are detected by their partial thromboplastin time (Thiagarajan et al., 1980; Love and Santoro, 1990). The anti-coagulant effect has been shown to be due to a specific reactivity of these antibodies with anionic phospholipids (Sammaritano et al., 1990). In addition, SLE patients have antibodies against native double-stranded DNA (dsDNA) which serve as diagnostic markers for SLE (Veinstein et al., 1983). Most patients with anti-phospholipid antibodies have SLE or a related autoimmune condition; some, however, have no other detectable disease and are considered as having a 'primary anti-phospholipid syndrome' (PAPS) (Asherson el al., 1989; Branch et al., 1990). In recent years the pathogenic significance of these antibodies has been established by inducing foetal loss in pregnant mice by passive transfer of human polyclonal antiphospholipid antibodies (Branch el al., 1990). PAPS has also been induced in naive mice by passive transfer of human polyclonal and mouse monoclonal anti-cardiolipin antibodies (Blank et al., 1991).

Anti-phospholipid or anticardiolipin antibodies also occur in a number of neurological conditions and their role has been emphasised in focal cerebral ischaemia, migraine, chorea, seizures and other conditions (Levine and Welch, 1987).

To date, the origin of anti-phospholipid or anti-dsDNA antibodies remains unknown. Studies in this regard appear to focus on the ligand binding properties of anti-phospholipid antibodies. Polyclonal anti-phospholipid antibodies from patients cross-react with the majority of anionic phospholipids (Lafer et al., 1981; Pengo et al., 1987). Attention however, was diverted to other ligands when monoclonal antibodies which bind to polynucleotides such as DNA were shown to bind also to cardiolipin and other anionic phospholipids (Schoenfeld et al., 1983; Rauch et al., 1984; Smeenk et al., 1987). This cross-reactivity is thought to be due to similarity in chemical structure of DNA and phospholipids which both contain phosphodiester-linked phosphate groups that are separated by three carbon atoms (Lafer et al., 1981). Lipoteichoic acids from gram-positive bacteria and endotoxin from gram-negative bacteria also contain phosphate esters and such molecules in foreign antigens are considered to be possible triggers for the generation of anti-phospholipid antibodies (Carroll et al., 1985).

Recently, the development of anti-dsDNA antibodies has been shown to correlate with frequent polyoma virus reactivations in some SLE patients. However, high titres of anti-dsDNA were also detected in the absence of viral DNA (Rekvig et al., 1997).

It has already been demonstrated herein that both cardiolipin and anti-dsDNA reactivities are encompassed within the binding specificities of anti-anti-TCR Vβ antibodies (see Table 3. For methods see experimental section). This is a characteristic of both the polyclonal antibodies from mice immunised with anti-TCR Vβ monoclonal antibodies and the anti-anti-TCR Vβ monoclonal reagents produced from such immunised mice. Furthermore, the said polyclonal mouse antisera had a powerful anticoagulant effect.

The potential mechanisms for the pathophysiological development of anti-anti-TCR Vβ antibodies have already been discussed (see page 12). The use of polyclonal or monoclonal anti-anti-TCR Vβ antibodies in preventing their development or the induction of protective antibodies has been pointed out (see page 25). Such methods should prevent the development of the combination of pathogenic anti-DNA and anti-phospholipid antibodies resulting in the alleviation of the diseases caused by these antibodies.

Application of the Invention to Further Diseases of Hormonal Dysregulation and Conditions Where β Cell Dysfunction or Hyperinsulinaemia and Insulin Resistance are Present As indicated previously the anti-anti-Vβ antibodies bind to islet α cells and other endocrine organs suggesting that its target molecules are involved in their secretory mechanisms. This would explain the finding that autoimmune endocrine disease can effect more than one organ in a single patient or autoantibodies against a clinically 'unaffected' organ can be present. The diseases which can coexist are hypothyroidism, hyperthyroidism (Grave's disease), diabetes mellitus, Addison's disease, primary hypogonadism, autoimmune gastritis and pernicious anaemia among others, the disease profile presumably reflecting the individual's genetic susceptibility.

The following are given by way of example and not limitation

Autoimmune Thyroid Disease

The incidence of autoimmune thyroid disease is substantially higher among patients with IDDM than in the general population (Payami and Thomson, 1989). Abnormal glucose tolerance and increased hepatic glucose production is often observed in hyperthyroidism (Wennlund et al. 1986). The accelerated gluconeogenesis is indicative of hyperglucagonaemia which was reported both in the basal state and after insulin infusion in 8 newly diagnosed hyperthyroid subjects by Moghetti et al. (1994). Also, the percentage decrease in glucagon levels after glucose administration or a meal is significantly less among hyperthyroid patients whether they are hyperglycaemic or not (Kabadi and Eisenstein, 1980; Bech et al. 1996). Insulin secretion is also dysregulated in hyperthyroid individuals. In a variety of conditions such as during a hyperglycaemic clamp (O'Meara el al. 1993), in the fasting state and after a meal (Bech et al. 1996) immunoreactive insulin concentrations were higher in thyrotoxic patients compared to controls. The rise in immunoreactive insulin was accounted for by increased proinsulin secretion. There is also evidence of increased secretion of ACTH (adrenocorticotrophic hormone), cortisol and growth hormone in hyperthyroidism (Moghetti et al. 1994; Gallagher et al. 1971) which is consistent with the hypothesis of dysregulation of the normal negative feedback control of hormone secretion due to the binding of anti-anti Vβ antibodies to target antigens on these organs. The dysregulated glucagon and insulin secretion in thyrotoxicosis is similar to the prediabetic and diabetic states; in analogous fashion the nocturnal TSH surge is blunted in most diabetic patients (Coiro et al. 1997).

Polycystic Ovary Syndrome (PCOS)

There is persistent enhanced early insulin response to intravenous glucose in women with PCOS which indicates a primary abnormality of insulin secretion (Holte, 1995). Such women also have a hyperglycaemic and hyperinsulinaemic response during an oral glucose tolerance test (OGTT) (Dunaif et al. 1987). Golland et al. (1990), however, reported that PCOS women had blunted glucagon responses in spite of hyperglycaemia during OGTT. This indicates that a second line glucose counterregulatory hormone i.e. epinephrine must be increased in PCOS women. Consistent with this is the adrenal hyperandrogenism found in half of the women with androgen excess (Ehrmann et al. 1992). The effect of adrenaline on steroidogenesis has been demonstrated both in perfused islolated adrenals and at the molecular level (Ehrhart-Bornstein et al. 1994; Guse-Behling et al. 1992). The histological demonstration by immunostaining of the intermingling of adrenal cortical cells within the entire adrenal medulla and vice versa confirms the role of the adrenal medulla as a regulator of adrenocortical function by a paracrine mechanism (Bornstein el al. 1994). The molecules recognised by the pathogenic autoantibodies described in this invention are abundantly represented on the adrenal medullary cells (FIG. 3). Such autoantibodies can be the cause of increased adrenaline secretion causing the adrenal hyperandrogenism in PCOS.

Adrenal hyperandrogenism frequently coincides with ovarian hyperandrogenism which is generally accompanied by LH augmentation. The abnormal pattern of ovarian steroidogenesis can only partly be explained by LH hyperstimulation of thecal cells and a hyperresponse to GnRH. Insulin and insulin like growth factors augment the androgenic response of thecal cells to LH by increasing levels of the rate determining enzymes in ovarian steroidogenesis and reversing LH induced downregulation of these enzymes (Hernandez et al. 1988; Magoffin et al. 1990). Therefore, hyperinsulinaemia has been proposed as the major candidate of ovarian dysregulation (Ehrmann et al. 1995).

Hyperinsulinaemia also appears to have a role in adrenal hyperandrogenism, however not directly but by synergising with ACTH stimulation (Moghetti et al. 1996). The secretion of pituitary glycoprotein hormones is pulsatile and the disruption of their pulses can alter reproductive function (Samuels et al. 1990; Santoro et al. 1986). It has been demonstrated that cultured pituitary lactotrophs express GPI-linked molecules which are rapidly hydrolysed by treatment with TRH (Benitez et al. 1995). Phospholipase C inhibition prevents the action of TRH and second messenger generation (Perez et al. 1997). The release of ACTH from rat anterior pituitary cells was shown to be prevented by inhibiting phospholipase C activity (Won and Orth, 1995). The effects of ACTH are also mimicked by phospholipase C (Foster and Veitl, 1995). Villa et al. (1995) reported that the accumulation of aldosterone in adrenocortical cells was inhibited in a dose-dependent manner by insoitol phosphoglycans demonstrating the regulatory role of these molecules. These observations demonstrate the far reaching effects of blocking sites of phospholipase C action by pathogenic anti-anti-Vβ autoantibodies described herein.

Obesity

Hyperinsulinaemia is characteristic of both juvenile and adult obesity. Le Stunff and Bougneres (1994) reported a 76% increase in insulin response to a standard meal in children with long or short duration of obesity; fasting insulin levels increased with duration of obesity. Obese children of long or short duration are also hyperglycaemic after a standard meal test compared to controls which is consistent with a report of increased gluconeogenesis in recently obese children (Le Stunff and Bougneres 1996).

Increased postprandial insulin increment has been shown to persist in women with massive obesity after normal body weight was achieved (Fletcher, et al. 1989). Therefore, hyperinsulinaemia appears to be a primary abnormality leading to obesity. In adult obesity, hyperinsulinaemia is also associated with increased levels of free fatty acids both during fasting and postprandial states (Golay et al. 1986). Increased gluconeogenesis and hyperinsulinaemia are likely to be the result of dysregulated glucagon secretion in obesity. Borghi et al. (1984) reported that glucose failed to suppress glucagon secretion in obese subjects. Golland el al. (1990) demonstrated that obese women had a significantly greater glucagon response at 60, 90 and 120 minutes after oral glucose loading than did non obese subjects. Both these observations demonstrate the lack of regulatory signals in pancreatic α cells analogous to prediabetic and diabetic conditions.

Cushing's Syndrome

This disease is commonly associated with glucose intolerance, diabetes, central obesity. hirsutism and elevated arterial blood pressure. The main diagnostic feature is hypercortisolism which may result from long standing ACTH hypersecretion in 20–40% of patients (Doppman el al. 1988); this can occur in the absence of a pituitary adenoma and increased cortisol secretion can be due to unilateral or bilateral adrenal hyperplasia with or without autonomously secreting micro or macro nodules (Hermus el al. 1988).

In a recent cross-sectional study of 90 patients with obesity and diabetes, the prevalence of Cushing's syndrome was reported to be 3.3% (Leibowitz et al. 1996). Pre-clinical and sub-clinical cases of Cushing's which present as poorly controlled diabetes add to this figure considerably. In analogous fashion mild chronic hypercortisolism has been reported in type 1 diabetes reflected by elevated fasting cortisol and urinary free cortisol and an increased response to ovine corticotropin-releasing hormone (Roy el al. 1993).

ACTH hypersecretion can occur in the absence of a pituitary adenoma but in the presence of hypercortisolaemia (Grant and Liddle, 1960) suggesting a dysregulation of the normal negative feedback control Several reports are indicative of the role of GPI-linked molecules and inositol phosphoglycans released by the activation of phospholipase C in the regulation of both pituitary hormone secretion and the secretion of the hormones that they stimulate from the adrenals, thyroid, gonads etc. (Fanjul el al. 1993; Shaver et al 1993; Villa et al. 1995;). It is therefore anticipated that the autoantibodies described herein will have pathogenic effects ranging from disruption of pulsatile secretion of hormones to inhibited or exaggerated secretion and even the formation of tumours as antibodies to GPI-linked molecules have also been shown to induce cell proliferation by causing loss of inhibitory input to activating signals (Robinson and Hederer, 1994; Benitez el al. 1995).

Metabolic Syndrome X and Cardiovascular Diseases

Syndrome X is the combination of hyperinsulinaemia, glucose intolerance, increased very low density lipoproteins (VLDL) and triglycerides decreased high density lipoproteins (HDL) and hypertension. Central obesity is also associated with this syndrome. The primary causal abnormality of this syndrome is considered to be insulin resistance (Reaven, 1988; Reaven, 1995). Hrnciar et al. (1992) estimated the presence of the Syndrome in 5–10% of the general population, in 15–30% of patients with arterial hypertension, in 65–90% of NIDDM, in 10–20% of hirsutic women and in 30–50% of patients with myocardial infarction. Piedrola et al. (1996) reported that 82.5% of 40 newly diagnosed coronary artery disease patients were insulin resistant and 27 of the 40 had an abnormal OGTT. Hyperinsulinaemia and insulin resistance correlate with the severity of peripheral vascular, coronary and carotid artery disease (Standl 1995; Reaven 1995) and are also involved in microvascular angina and exercise induced coronary ischaemia (Vertergaard et al. 1995).

In a survey of cardiovascular disease and Syndrome X in 2930 subjects Ferrannini et al. (1991) reported that isolated forms of each condition of the syndrome were rare but were always associated with hyperinsulinaemia suggesting that this is the key feature of the syndrome. Sowers et al., (1993) have also suggested that hyperinsulinaemia may contribute to the development of hypertension by promoting atherosclerosis and vascular remodelling. Insulin resistance has been observed to be associated with increased carotid wall thickness (Suzuki et al. 1996) and carotid artery plaques (Laakso et al. 1991). A recent prospective population-based study by Salonen et al. (1998) supports the hypothesis implicating insulin resistance in the etiology of hypertension and dyslipidemia. Moller et al. (1996) demonstrated that a pure defect in muscle insulin receptor-mediated signalling caused insulin resistance, hyperinsulinaemia, obesity, increased plasma triglycerides and free fatty acids in transgenic mice. In NIDDM muscle biopsies indicate a generalised deficiency of inositol phosphoglycan mediators of insulin action (Asplin et al. 1993). The pathogenic antibodies described herein could cross-react with such mediators and induce insulin resistance both by downregulating them and also by disrupting pulsatile secretion of insulin.

Immunologically Mediated Multisystem Diseases

Hyperinsulinaemia and insulin resistance have also been been shown to be prominent in multisystem diseases such as systemic lupus erythematosus and progressive systemic sclerosis. The serum fasting insulin levels in 21 such patients were double that of normal controls and they had significantly higher triglycerides and lower HDL cholesterol levels (Mateucci et al. 1996)

Cancer

Hyperinsulinaemia, a diabetic pattern of glucose tolerance, an increased rate of HGP and insulin resistance are associated with many cancers including breast, colorectal, gastrointestinal, sarcoma, endometrial, prostate, head neck and lung (Tayek 1992; Copeland, Leinster et al 1987; Copeland, Al-Sumidaie et al. 1987; Tayek 1995; Nagamani et al. 1988). Bruning et al. (1992) demonstrated that the log relative risk of breast cancer was linearly related to the log C-peptide levels. This was independent of BMI (body mass index) or WHR (waist to hip ratio); the 223 women with stage I or stage II breast cancer were insulin resistant and had significantly higher C-peptide levels than the 441 controls. In a recent study of 2569 histologically confirmed cases of breast cancer and 2588 control women an association of breast cancer with late onset diabetes has also been noted (Talamani et al. 1997). The direct role of insulin in promoting tumours has been shown in a rat model of colon tumours (Tran et al. 1996).

Cancer cachexia also appears to be characterised by glucose intolerance, postabsorptive hyperglycaemia, reduced total body glucose utilisation consistent with insulin resistance and augmented peripheral lactate production. The insulin to glucagon ratio is also reduced; increased circulating glucagon levels are associated with the tumour-bearing state (Cersosimo el al. 1991) which is consistent with the increased HGP in many cancers. Bartlett et al. (1995) demonstrated that increasing the insulin/glucagon ratio by hormone therapy selectively supported host anabolism and inhibited tumour growth kinetics in a rat model. Therefore, preventing the development of the diabetogenic complex of metabolic derangements will reduce the incidence of cancers and alleviate symptoms of cancer cachexia.

Diagnostic, Prophylactic and Therapeutic Uses of the Invention

The following are given by way of illustration and not limitation.

The invention will be applied to the prevention and treatment of autoimmune and related diseases by injecting pharmaceutical preparations of the monclonal or polyclonal anti-anti-Vβ antibodies or equivalent ligands, the peptide fragments or molecules recognised by these antibodies and functionally active vectors containing RNA or DNA sequences coding for such peptides or molecules.

Injection of antibody will be designed to prevent the development of autoantibodies of the same specificity by feedback mechanisms suppressing existing B cells or by an idiotypic network of antibody development giving rise to protective antibodies (see pages 17 and 25). Soluble peptides or other target molecules recognised by the pathogenic anti-anti-Vβ antibodies will also be used to induce low dose tolerance, the specific blocking of already activated B cells (see page 17) or in larger predetermined doses to block the action of the mediators of specific nephropathy such as TGF-β (see page 27). Vectors containing appropriate nucleic acid sequences will also be injected by predetermined regimens to allow the long term in vivo secretion of soluble products which will function as tolerogens. The peptides, proteins or other molecules recognised by the anti-anti-Vβ pathogenic antibodies and the anti-Vβ immunogens used in the generation of these antibodies will be used in the development of diagnostic kits to detect the presence of auto-anti-anti-Vβ antibodies in blood, plasma, serum, saliva or other body fluids to ascertain susceptibility to autoimmune disease or as prognostic indicators of the progression of disease or treatment efficacy.

Various aspects and embodiments of the present invention will now be described in more detail by way of example. It will be appreciated that modification of detail may be made without departing from the scope of the invention.

BRIEF DESCRIPTION OF THE FIGURES

FIG. 6. Sequence of the ESRP1 gene (SEQ ID NO:1).

FIG. 7. Predicted protein sequence for the ESRP1 proteins (SEQ ID NOS:2–4).

EXPERIMENTAL

Figure 1:
FIG. 1. Staining of a normal human pancreatic section with a monoclonal anti-anti-Vβ antibody detected by a fluoresceinated second reagent.
Figure 2:
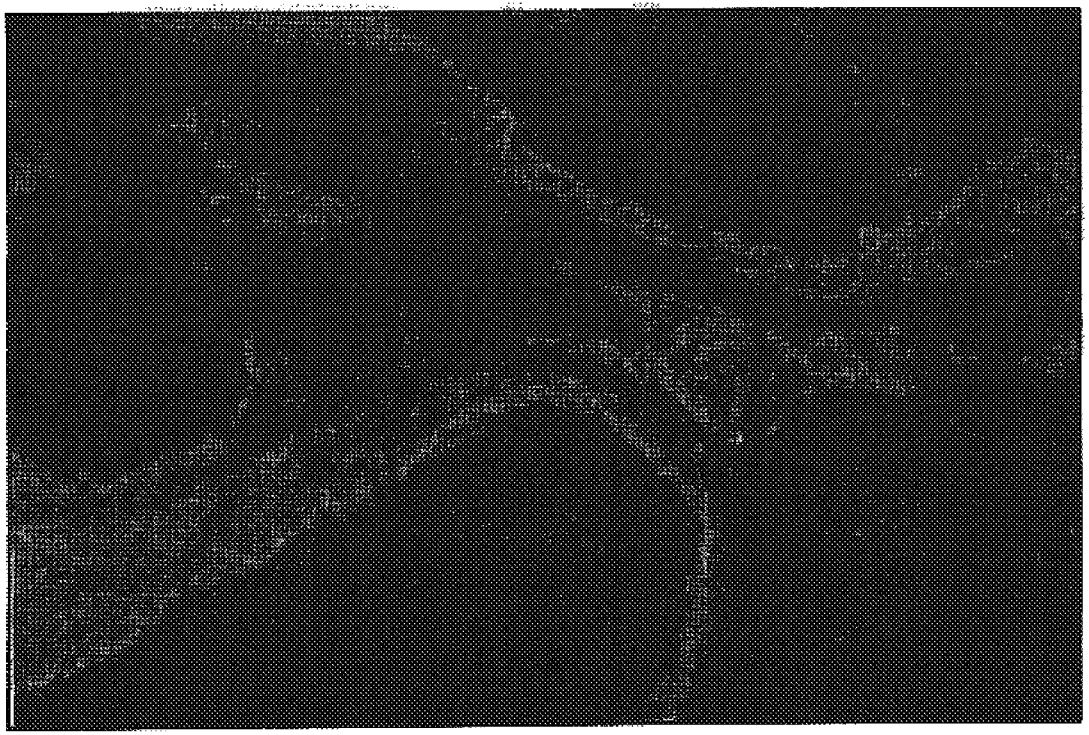
FIG. 2. Staining of a normal human thyroid section with a monoclonal anti-anti-Vβ antibody detected by a fluoresceinated second reagent.
Figure 3:
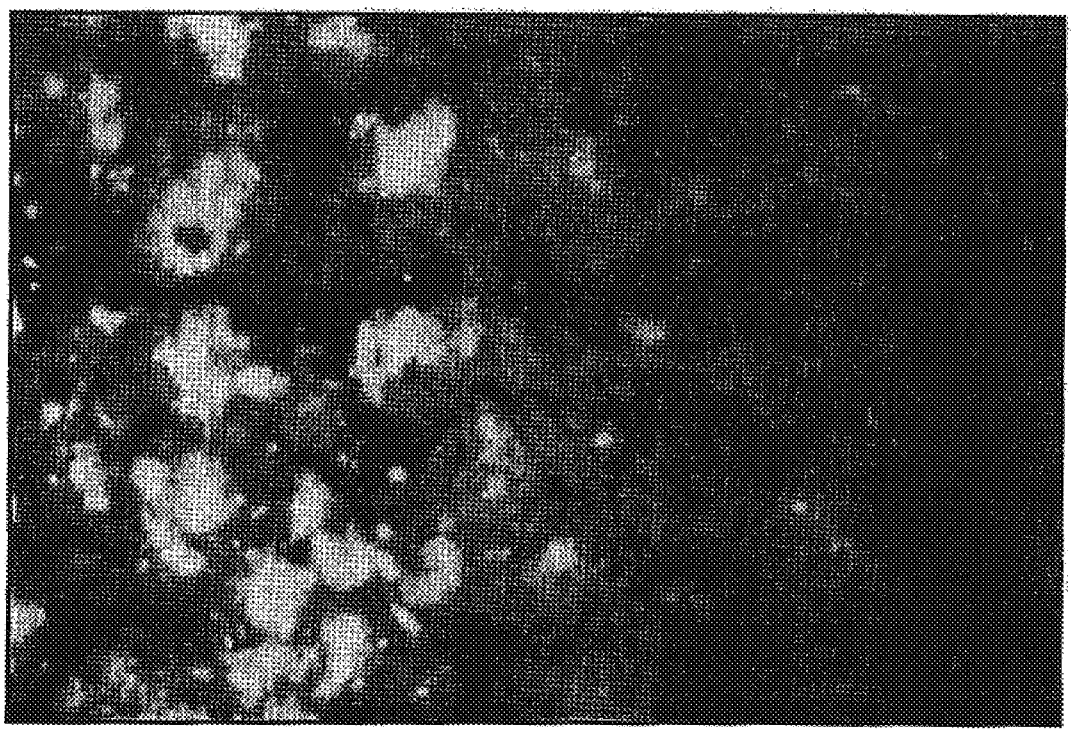
FIG. 3. Staining of a normal human adrenal section with a monoclonal anti-anti-Vβ antibody detected by a fluoresceinated second reagent.
Figure 4:
FIG. 4. Staining of a normal human intestine section with a monoclonal anti-anti-Vβ antibody detected by a fluoresceinated second reagent.

The following examples are given by way of illustration not by way of limitation.

Development of Monoclonal Antibodies

Mice were immunised intraperitoneally (ip) with 4 weekly injections of 0.1 ml monoclonal antibody hybridoma culture supernatant against TCR Vβ specificities. The spleens were then removed and single cell suspensions were prepared. The cells were fused with Sp2 myeloma cells using standard techniques known to workers in the field and related fields. The antibody producing clones were identified in ELISA using peroxidase conjugated anti-Ig reagents. The clones were further screened against the immunising reagent, double and single stranded DNA and anionic phospholipids. Methods used were standard techniques known to workers in the field.

Detection of Anti-phospholipid Antibodies

Flexible 96 well flat bottom plates (Falcon, Becton-Dickinson) were coated with 50 µl of 50 µg/ml in ethanol of cardiolipin, phosphatidylcholine, phosphatidylserine and 50 µg/ml in methanol of phosphatidylinositol (Sigma). Control wells were coated with diluent alone. The plates were left at 4° C. until evaporation. Unbound sites were blocked with 0.1% human serum albumin (HSA) in phosphate buffered saline(PBS). The plates were washed with PBS containing 0.05% Tween 20 (RTM) and incubated with serial dilutions of sera in PBS Tween (RTM) or MoAb culture supernatants. After incubation for 1 hour at 37° C. or overnight at 4° C., the plates were washed again as above and the bound antibodies were detected using a 1:500 dilution of biotinylated anti-mouse Ig (Amersham International plc), incubated for 30 minutes at 37° C. followed after appropriate washing by a further 30 minutes incubation at 37° C. with 1:500 streptavidin-biotinylated horseradish peroxidase complex (Amersham International plc). O-phenylenediamine (Sigma) was used as substrate and the colour was read at 450 nm using an Anthos ELISA reader.

Detection of Anti-DNA Antibodies

Wells of 96 well flat bottom flexible plates were coated first with 50 µg/ml poly-1-lysine in water by incubating for 1 hour at room temperature. After discarding the poly-1-lysine solution, 50 µl of single stranded or double stranded DNA (Sigma) solution 10 µg/ml in PBS containing 1 mM EDTA was added to each well and the plates incubated for 1 hour at room temperature. The plates were washed in PBS. Remaining binding sites were blocked with 0.1% HSA in PBS. The plates were washed with PBS containing 0.05% Tween 20 (RTM) and incubated with serial dilutions of sera or MoAb culture supernatants. Binding of antibody was detected as described above for anti-phospholipid antibodies.

Testing for the Anticoagulant Effect of Anti-anti-Vβ Antibodies

Antisera from several strains of inbred mice immunised by various anti-TCR Vβ monoclonal antibodies were tested. Five µl of each antiserum was mixed with 95 µl hard spun normal human plasma and incubated at 37° C. for 1 hour. To this was added 100 µl of appropriately diluted Russell's viper venom (Diagen) and 100 µl of diluted platelet substitute (Diagen) and incubated for 30 seconds. 100 µl of 0.025M CaCl$_2$ was then added and the clotting time measured. Clotting time in the presence of normal mouse serum was approximately 55 seconds while in the presence of the said immune sera the clotting time ranged from 10 to 30 minutes. A control murine antiserum did not prolong the clotting time above that of normal mouse serum.

Staining of Diabetic Pancreas Sections

Pancreas sections from a recently diagnosed insulin dependent diabetic patient who died accidentally (from diabetes unrelated causes) and pancreas sections from normal cadaveric organ donors were stained with anti-anti-Vβ monoclonal antibodies. The normal pancreas sections showed intraislet staining as expected (see FIG. 1) but the diabetic pancreas either did not stain at all or stained very faintly. This indicates that in this patient the relevant α cell antigens were downregulated or switched off.

Figure 5:
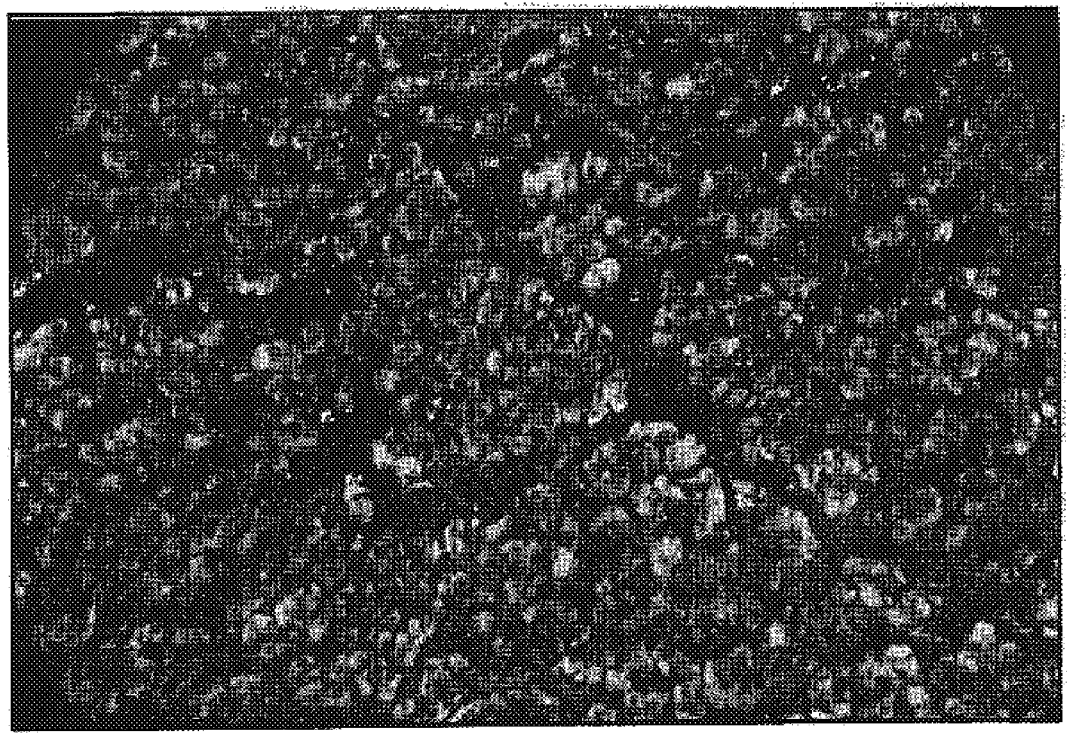
FIG. 5. Staining with an anti-anti-Vβ monoclonal antibody and fluoresceinated second reagent of a pancreas section from a child who died at diagnosis of diabetes from uncontrolled ketoacidosis.

In contrast to this, anti-anti-Vβ staining of pancreatic sections from three children who died at diagnosis from keto-acidosis showed a proliferation of positive staining cells outside the confines of islets (FIG. 5). This may have been due to large amounts of autoantibody reacting in vivo with the laminin binding-like protein or other target proteins causing proliferation and migration of the α cells outside of the islets.

Both the scenarios described above could fit into a spectrum of responses by individuals of different genetic constitution to cause fulminant uncontrolled keto-acidosis and death or IDDM in individuals with fragile β cells and NIDDM in those with more robust β cells.

Effect of Monoclonal Anti-anti-V Beta Antibodies on Intact Human Islets in Vitro Separated human islets from a cadaveric organ donor were washed in RPMI 1640 medium containing 10% foetal calf serum and cultured at a concentration of approximately 200 islets per well in the same medium in 24-well plates. Three days later the medium from duplicate wells was carefully removed and stored at −20° C. The control wells were then cultured with medium alone and the test with hybridoma culture supernatant containing anti-anti-Vβ diluted with an equal volume of fresh medium. After 24 hrs the supernatant in each well was removed and stored as above and replenished with medium alone or hybridoma supernatant diluted as above. This was repeated daily for 2 weeks except that the supernatants were not removed during the week-end. At the end of the experimental period, the insulin in the stored samples was measured using a DAKO insulin kit according to the manufacturer's instructions. The results demonstrated that the insulin levels in the test and control wells were almost identical at the start of the experiment. Twenty four hours after the addition of antibody the insulin level in the test well rose considerably higher than in the control well. On the third day insulin secretion in the antibody containing well dropped to approximately 50% of the control. On the fourth day insulin secretion in the test well was again above the control well, while on the fifth day the levels were similar. The results given in optical density (OD) readings in Table 1 demonstrate that while insulin release in the control well was fairly constant, there were sharp fluctuations in the test well during the first experimental week. During the second week insulin in the test well dropped and by the tenth day no secretion could be detected while in the control well secretion was well above the background OD reading. Even though further measurements of secretion in the control wells were not carried out, the slow rate of decline of insulin secretion in the control well indicates that secretion could have carried on for several more days.

TABLE 1

Effect of monoclonal anti-anti-TCR Vβ antibodies on human islets in vitro

| | Optical Density | |
|---|---|---|
| Day No. | Test | Control |
| 1 | 2.117, 2.063 | 2.042, 1.848 |
| 2 | 2.784, 2.751 | 2.143, 2.044 |
| 3 | 1.236, 1.057 | 2.256, 2.240 |
| 4 | 2.513. 2,377 | 2.124, 2.187 |
| 5 | 2.446, 2.450 | 2.506, 2.545 |
| 8 | 0.699 | 1.114 |
| 9 | 0.777 | 1.049 |
| 10 | 0.585 | 0.979 |
| 11 | 0.482 | 0.842 |

Optical density was measured using an Anthos 2001 plate reader at 450 nm with reference filter at 650 nm. Optical density for culture medium was 0.532.

Demonstration of Naturally Occurring Anti-anti-Vβ Autoantibodies in Human Sera

Anti-anti-Vβ antibodies were generated from spleens of mice immunised with culture supernatant from hybridoma cell lines secreting anti-TCR Vβ antibodies. These anti-anti-Vβ monoclonals were shown to bind to the anti-Vβ immunogen in ELISA; therefore the use of this immunising reagent as antigen to detect the presence of auto anti-anti-Vβ antibodies in human sera was examined. The anti-Vβ immunogen was used to coat 96-well flat-bottomed plates overnight, the unbound sites blocked and human sera added in 1/30 dilution to the wells. After 2 hrs, incubation the plates were washed and the binding of the human serum detected using a peroxidase conjugated anti-human Ig.

Table 2 depicts results with sera obtained from three prediabetic donors who subsequently became diabetic. The serum samples from donor 3 were fortuitously spaced and demonstrate the highest level of autoantibody a year before diagnosis. A rise in the index of binding (Test OD/Control OD) from 4.4 to 6.1 occurred within 7 months of the first sample and dropped to 2.9, 2 months before diagnosis. This demonstrates the transient nature of this autoantibody and that it may not be long-term persistence that leads to disease development but perhaps several episodes of rises in titre due to viral or other infections leading to T-cell proliferation and the appearance of abnormal GPI-linked TCR Vβ chains. The autoantibodies appear to have persisted, however, for at least seven months to a year at high levels in patient 3. This may have led to downregulation of the signalling molecules on the pancreatic, cells as mentioned earlier (pages 25 and 40).

TABLE 2

Anti-anti-TCR Vβ autoantibodies are present in human sera

| | | Diagnosis | Optical Density | | |
|---|---|---|---|---|---|
| Donor No. | Serum date | of IDDM date | Test antigen | Test/ Control | Control(Medium) |
| 1 | 5/1989 | 1/1991 | 0.082, 0.080 | | 0.124, 0.134 |
| 2 | 2/1989 | 1/1993 | 0.087, 0.076 | 1.5 | 0.058, 0.054 |
|  | 6/1989 |  | 0.079, 0.074 |  | 0.076, 0.063 |
| 3 | 5/1987 | 12/1988 | 0.074, 0.072 | 4.4 | 0.016, 0.017 |
|  | 12/1987 |  | 0.109, 0.097 | 6.1 | 0.016, 0.018 |
|  | 10/1988 |  | 0.060, 0.057 | 2.9 | 0.021, 0.019 |

The test antigen was culture supernatant from an anti-TCR Vβ producing monoclonal cell line.

The Test/Control index was obtained by dividing mean OD test by mean OD control.

TABLE 3

Binding specificities of monoclonal anti-anti-TCR Vβ antibodies

| | Optical Density | |
|---|---|---|
| Well coat reagent | Experiment 1 | Experiment 2 |
| Anti-TCR Vβ (Immunogen) | 0.413 | 0.399 |
| Culture medium (Control) | 0.046 | 0.040 |
| Cardiolipin in ethanol | 1.002 | 0.998 |
| Ethanol (Control) | 0.156 | 0.126 |
| dsDNA | 0.210 | 0.242 |
| Poly-l-lysine (Control) | 0.119 | 0.129 |

Optical density was measured using an Anthos 2001 plate reader at 450 nm with reference filter at 650 nm. The anti-TCR Vβ was used as culture supernatant.

Screening of Pancreas Library with Monoclonal Antibodies (MoAbs)

Libraries in λgt11 have DNA sequences inserted into the EcoR1 site and can be expressed as fusion proteins under the control of the lac promoter. Therefore they can be screened with antibodies.

In the present case, the method described by Webster et al., 1992 (Methods in Molecular Biology vol 10. Immunochemical protocols Ed. M. Manson) were used to screen a λgt11 human pancreas library (Promega). Briefly, the bacterial strain Y1090 was transfected with bacteriophage mixed with molten agarose and plated onto media plates. The agarose-embedded bacteria grow and make a continuous lawn except where phage lyse the cells to form clear plaques. At appropriate dilutions of phage, each discreet plaque arises from one phage infecting one bacterium. Agar plates are then overlayed with a sheet of nitrocellulose membrane (Protran BA85 0.45 μm, 82 mm, Schleicher and Schuell) that has been soaked in isopropyl β-D-thiogalactoside (IPTG) which induces the β-galactosidase gene (within the λgt11) into which the cDNA has been inserted in the unique EcoR1site. If the cDNA is in the correct reading frame and orientation, a fusion protein will be produced which is an extension of the β-galactosidase protein at the carboxyterminus. Membrane-overlayed plates are then incubated at a slightly lower temperature allowing the production of the fusion protein to increase. The membranes are then removed and washed to remove bacterial debris and probed with the MoAbs to detect cDNA clones coding for protein sequences that react with the antibodies. For this procedure, the membranes were first incubated in wash solution (5% milk powder in PBS containing 0.02% Tween (RTM) 20) for 30 minutes to prevent nonspecific binding of antibody. They were then rinsed in wash solution and placed in petri dishes containing neat MoAb and placed on a shaker for 2–3 hours. The antibody was then removed and the membrane washed in 3 changes of wash buffer for a total of 30 minutes on the shaker. The wash buffer was then removed and the membranes were immersed in a suitably diluted horse radish peroxidase labelled anti-mouse antibody (Sigma) for 1 hour on the shaker. The antibody solution was then discarded and the membranes washed with 3 changes of wash buffer over 30 minutes on a shaker. Antibody binding was then detected using ECL (enhanced chemiluminescence) reagents (Amersham Life Sciences). Equal volumes of the 2 reagents were mixed and overlayed on the protein side of the membrane for 1 minute. The excess detection reagent was then drained and the membranes covered in Saran wrap and exposed to autoradiography film (Hyperfilm™-ECL) in a cassette. The films were developed and matched to the agar plates containing the plaques. Positive plaques were picked out using pasteur pipettes and transferred to 0.5 ml of phage eluant (SM:0.1M NaCl, 0.01M MgSO$_4$.7H$_2$O, 0.05M Tris base, 0.01%w/v gelatin (swine skin Type 1, adjusted to pH 7.5) containing 50 µl chloroform as preservative. Positive plaques were rescreened until all plaques on the membrane were positive.

Polymerase Chain Reaction (PCR) Amplification of cDNA Clones

Eight cDNA clones, plaque purified as described previously, were amplified using the following amplification mix: Taq Plus (Stratagene) 10×Low Salt Reaction Buffer 5 µl dNTPs (Pharmacia) each 200 µM Forward and Reverse primers each 25 pM (Forward: GTA GAC CCA AGC TTT CCT GGA GCA TGT CAG TAT AGG AGG (SEQ ID NO:5); Reverse: CTG CTC GAG CGG CCG CAT GCT AGC GAC CGG CGC TCA GCT GG (SEQ ID NO:6); Perkin Elmer) Taq Plus DNA polymerase (Stratagene) 1 Unit; cDNA template 2 µl; dH$_2$O up to 50 µl.

The DNA polymerase was added during a 7 minute pre-run at 94° C., i.e. hot start. The reaction mix was overlayed with 100 µl mineral oil. Tubes were placed in a DNA Thermal Cycler (Perkin-Elmer Cetus, Emeryville, Calif.) programmed as follows:

94° C. (denaturing) 1 min, 55° C. (annealing) 2 min, 72° C. (extension) 3 min, for 36 cycles. The last extension was 7 minutes. The PCR products were stored at 4° C. until analysis.

Analysis of PCR Products

A 1% agarose gel containing 0.5 µg/ml ethidium bromide was prepared in TAE buffer (Tris base 242 g., glacial acetic acid 57.1 ml, 0.5 M EDTA (pH 8.0) 100 ml, dH$_2$O up to 1000 ml). Ten µl of each PCR product was loaded with 2 µl of sample buffer. Two µl of 100 base pair and 1 kb DNA ladder (Gibco, BRL) were also loaded on either side of the PCR products for reference. The gels were run at 100 V for 1 hour. The PCR products were visualised under UV light and photographed using Polaroid (RTM) 667 film (Polaroid, St. Albans, UK)

DNA Sequencing

The identity of the PCR products were checked by sequencing using ABI PRISM Dye Terminator Cycle Sequencing ready reaction kit and ABI 373A Sequencer (Applied Biosystems, Perkin-Elmer, Foster City, Calif.).

The cycle sequencing reaction mix was as follows:

terminator ready reaction mix—8 µl, PCR products (10 to 30 ng./µl) 3–6 µl, primer 3.2 pM, dH$_2$O up to 20 µl overlayed with 50 µl light mineral oil. The tubes were placed in the DNA Thermal Cycler and run according to the following program: 96° C. for 30 seconds, 50° C. for 15 seconds, 60° C. for 4 minutes repeated for 25 cycles. The 20 µl extension products were transferred to 1.5 ml microcentrifuge tubes and 2 1 of 3M sodium acetate (pH 4.6) and 50 µl of 95% ethanol were added. The tubes were vortexed and placed on ice for 10 minutes, then centrifuged at 13,000 rpm for 15–30 minutes. The ethanol solution was discarded and the pellet washed in 75% ethanol. The tubes were respun and the ethanol solution was carefully removed and the pellet dried in a vacuum centrifuge.

Preparation and Loading of Samples

The dried sample pellets were resuspended in 6 µl of loading buffer (deionized formamide 5 volumes; 50 mg/ml blue dextran in 25 mM EDTA (pH 8.0) 1 volume). The samples were vortexed and centrifuged. They were then heated at 90° C. for 2 minutes and kept in ice until ready to load. The samples were loaded on to a 6% acrylamide gel pre-run for 30 minutes at 1500–2000 V. After loading they were electrophoresed at 2000V for 12 hours. The sequence data were analysed by computer.

Eight cDNA clones were purified and sequenced. As discussed above, clones 1.1, 1.2 and 1.3 were found to code for a secretogranin 1 like protein; clones 3.1, 4.1 and 5.1 coded for a 67 kd laminin receptor-like protein; clone 5.2 coded for a new molecule that has been named ESRP1 (endocrine secretion regulatory protein 1. The nucleotide sequence of ESRP1 is given in FIG. 6, and the predicted amino acid sequence that it encodes is shown in FIG. 7.

Cloning of cDNAs into a Eukaryotic Expression Vector (pCR™3-Uni, Invitrogen)

This was done using the unidirectional eukaryotic TA cloning kit (Invitrogen). The linearised vector pCR™3-Uni_does not have a 5'-phosphate group on the left arm and therefore will only ligate PCR products with a 5'-phosphate. The forward primer used in the amplification of the cDNA was therefore phosphorylated prior to the ligation reaction as follows: Forward PCR primer (50–100 µM) 0.5–1 µg, 10×-kinase buffer 1 µl, 10 mM ATP 1 µl, sterile water to 9 µl, T4 polynucleotide kinase (10 Units/µl) 1 µl were gently mixed in a sterile 0.5 ml microcentrifuge tube and incubated at 37° C. for 30–40 minutes and at 94° C. for 5 minutes and then placed on ice. The phosphorylated forward primer was then used immediately to make a PCR product as described previously and 10 µl of PCR product was analysed on an agarose gel.

The ligation reaction was set up as follows: fresh PCR product (approximately 10 ng) 0.5–1.0 µl, sterile water 5.0–5.5 µl, 10×ligation buffer 1 µl, pCR™ 3-Uni vector (60 ng) 2 µl, T4 DNA ligase 1 µl. The mixture was incubated at 14° C. for 4 hours or overnight.

The ligation reactions were transformed into Top 10F' cells (One Shot). One shot cells were thawed on ice and 2

µl of 0.5M β-mercaptoethanol was added to the vial. The cells were mixed with 1–2 µl of the ligation reaction and incubated on ice for 30 minutes. The cells were then heat shocked at 42° C. for exactly 30 seconds. SOC medium, 450 µl was then added to the vials. They were then incubated on their side at 37° C. for 1 hour at 225 rpm in an incubator. Transformed cells were plated on LB plates with ampicillin and incubated overnight at 37° C. Transformants were picked and cultured for the isolation of plasmids.

Plasmid Purification

Transformed Top 10F' cells were cultured in LB broth containing ampicillin and plasmid DNA was purified using Wizard Miniprep (Promega) kits or the Endotoxin Free Plasmid Kit (Qiagen) for ultra pure DNA. Plasmid DNA was analysed for presence and orientation of insert by PCR and sequencing.

REFERENCES

Ammala, C., Ashcroft, F. M. and Rorsman, P. (1993). Nature 363, 356–358.

Asherson, R. A., Khamashta, M. A., Ordi-Ros, J., Derksen, R. H. W. M., Machin. S. J., Barquinero, J., Outt, H. H., Harris, E. N., Vilardell-Torres, M. and Hughes. G. R. V. (1989). Medicine (Baltimore) 68:366–374.

Asplin, I., Galasko, G. and Lamer, J. (1993). Proc. Natl. Acad. Sci. 90:5924–5928.

Barrou, Z., Seaquist, E. R. and Robertson, R. P. (1994). Diabetes 43, 661–666.

Barsky, S. H., Rao, C. N., Hyams, D. and Liotta, L. A. (1984). Breast Cancer Res. Treat. 4, 181–188.

Bartlett D. L., Charland S. L., Torosian M. H. (1995). Surgery 118:87–97.

Bech K., Damsbo P., Eldrup E., Bech-Nielson, H., Roder M. E., Hartling S. G., Volund A. and Madsbad S. (1996). Clin. Endocrinol. 44:59–66.

Bell, L. M., Solomon, K. R., Gold, J. P. and Tan K-N. (1994). J. Biol. Chem. 269, 2758–22763.

Bendelac, A., Camaud, C., Boitard, C. and Bach, J. F. (1987). J. Exp. Med. 166, 823–832

Benedum. U. M., Lamoureux, A., Konecki, D. S., Rosa, P., Hillie, A., Baeuerle, P. A., Frank, R., Lottspeich, F., Mallet, J. and Huttner, W. B. (1987). EMBO J. 6, 1203–1211.

Benitez L., Fanjul L. F., Ruiz de Galarreta C. M., Quintana Aguiar J., Gonzalez Reyes J., Hernandez I., Santana Delgado P., Cabrera Oliva J., Alonso Solis R. and Estevez Rosas I. (1995). Neuroscience Lett. 187:3740.

Bergsten, P. (1995). Am. J. Physiol. 268, E282–287.

Bergsten, P., Grapengiesser. F., Gylfe, E., Tengholm, A. and Hellman, B. (1994). J. Biol. Chem. 269, 8749–8753.

Blank, M., Cohen. J., Toder, V. and Schoenfeld, Y. (1991). Proc. Natl. Acad. Sci. USA 88,3069–3073.

Border, W. A., Okuda, S., Languino, L. R., Sporn M. B. and Ruoslahti, E. (1990). Nature 346, 71–374.

Borghi V. C., Wajchenberg B. L. and Cesar F. P. (1984). Metabolism 33:1068–1074.

Bornstein S. R., Gonzalez-Hernandez J. A., Ehrhart-Bornstein M., Adler G. and Scherbaum W. A. (1994). J. Clin. Endocrinol. Metab. 78: 225–232.

Bork, P. and Sander, C. (1992). FEBS Lett. 300, 237–240.

Bougneres, P. F., Carel, J. C., Castano, L., Boitard, C., Gardin, J. P., Landais, P., Ilors, J., Mihatsch, M. J., Paillard, M., Chaussain, J. L. and Bach, J. F. (1988). N. Eng. J. Med. 318, 663–670.

Boyd, A. E. III. (1992). J. Cell. Biochem. 48, 234–241.

Branch, D. W., Dudley, D. J., Mitchell, M. D., Creighton, K. A., Abbot, T. M., Hammond, E. H. and Daynes, R. A. (1990). Am. J. Obstet. Gynecol. 163, 210–215.

Brand, C. L., Jorgensen, P. N., Knigge, U., Warberg, J., Svendsen, I., Kristensen, J. S. and Holst, J. J. (1995). Am. J. Physiol. 269 (Endocrinol. Metab.) 32, E469–477.

Brett, S. S., Baxter, G., Cooper, H., Rowan, W., Regan, T., Tite, J. and Rapson, N. (1996). Int. Immunol. 8, 325–334.

Bruning P. F., Boonfrer J. M., vanNoord P. A., Hart A. A., deJong-Bakkar M., Nooijen W. J. (1992). Int. J. Cancer. 52:511–516.

Carroll, P., Stafford, D., Schwartz, S. and Stollar, B. D. (1985). J. Immunol. 135, 1086–1090.

Castano, L. and Eisenbarth, G. S. (1990). Ann. Rev. Immuol. 8, 647–680.

Cersosimo E., Pisters P. W. Pesola G., Rogatko A., Vydelingum N. A., Bajorunas D., Brennan M. F. (1991). Surgery 109: 459–467.

Chan, B. L. Lisanti, M. P., Rodriguez-Boulan, E. and Saltiel, A. R. (1988). Science 1670–1672.

Chen, M., Tempst, P. and Yanker, B. A. (1992). J. Neurochem. 58, 1691–1697.

Coiro V., Volpi R., Marchesi C., Capretti L., Speronti G., Caffarri G. and Chiodera P. (1997). Clin. Endocrinol. 47:305–310.

Copeland G. P., Al-Sumidaie A. M., Leinster S. J., Davis J. C., Hipkin L. H. (1987). Eur J. Surg. Oncol. 13: 11–16.

Copeland G. P., Leinster S. J., Davis J. C., Hipkin L. J. (1987). Br. J. Surg. 74: 1031–1035.

Cowchock, F. S., Smith, J. B. and Gocial, B. (1986). Am. J. Obstet. Gynecol. 155,1002–1010.

Cryer, P. E. (1995). Proc. Assoc. Am. Physicians 107, 67–70.

Cryer, P. E. (1994). Diabetes 43, 1378–1389.

Dagogo-Jack, S., Craft, S., Cryer P. (1993). J. Clin. Invest. 91, 819–828.

Davey, M. G. (1979). Vox. Sang. 36, 50–64.

Deeney, J. T., Cunningham, B. A., Cliheda, S., Bokvist, K., Juntti-Berggren, L., Lam, K., Korchak, H. M., Corkey, B. E. and Berggren, P. O. (1996). J. Biol. Chem. 271, 18154–18160.

Dittie, A. and Kern, H. E. (1992). Eur. J. Cell. Biol. 58, 243–258.

Doppman J. L., Miller D. L., Dwyer A. J. et al. (1988). Radiology 166:347–352.

Dunaif A., Graf M., Mandeli J., Laumas V. and Dobrjaansky A. (1987). J. Clin. Endocrinol. Metab. 65:499–507.

Dunaif A., Segal K. R., Futterweitt W. and Dobrjansky A. (1989). Diabetes 38:1165–1174.

Ehrhart-Bornstien M., Bornstein S. R., Guse-Behling H., Stromeyer H. G., Rasmussen T. N., Scherbaum W. A. Adler G. and Holst J. J. (1994). Neuroendocrinol. 59:406–412.

Ehrmann D. A., Rosenfield R. L., Barnes R. B., Brigell D. F. and Sheikh Z. (1992). N. Engl. J. Med. 327: 157–162.

Ehrmann D. A., Barnes R. B. and Rosenfield R. L. (1995). Endocr. Rev. 16: 322–353.

Fanjul L. F., Marrero I., Estevez F., Gonzalez J., Quintana J., Santana P., Ruiz de Galarreta C. M. (1993). J. Cell. Physiol. 155:273–281.

Ferrannini E., Haffner S. M., Mitchell B. D. and Stern M. P. (1991). Diabetologia 34:416–422.

Fletcher J. M., McNurlan M. A., McHardy K. C. (1989). Eur. J. Clin. Nutr. 43: 539–545.

Forss-Petter, S., Danielson, P., Battenberg, E., Bloom, F. and Sutcliffe, J. G. (1989). J. Mol. Neurosci. 1, 63–75.

Foster R. H. and Veiti S., (1995). Gen. Pharmacol. 26:955–959.

Fukushima, D., Butzow, R., Hildebrand, A. and Ruoslahti, E. (1993). J. Biol. Chem. 268, 22710–22715.

Gallagher T. F., Hellman L., Finkelstein J., Yoshida K., Weitzman E. D., Roffwang H. D. and Fukushima D. K. (1971). J. Endocrinol. Metab. 43:919–927.

Gepts, W. (1995). Diabetes 14, 619–663.

Giovannucci E. (1995). Cancer Causes Control. 6:164–179.

Golay A., Swislocki L. M., Chen Y.-D. I., Jaspan J. B. and Reaven M. (1986). J. Clin. Endocrionol. Metab. 63:481–484.

Golland I. M., Vaughan Williams, Shalet S. M., Laing I. And Elstein M. (1990). Clin. Endocrinol. 33:645–651.

Grant W. and Liddle M. D, (1960). J. Clin. Endocrinol. Metab. 20:1539–1560.

Guillausseau, P. J. (1994). Diabete Metab. 20. 325–329.

Guse-Behling H., Ehrhart-Bomstein M:, Bornstein S. R., Waterman M. R., Scherabaum W. A. and Adler G. (1992). J. Endocrinol. 135:229–237.

Harris, E. N., Gharavi, A. N., Boey, M. L. Patel, S., Macworth-Young, C. G. and Hughes, G. R. V. (1983). Lancet ii, 1211–1214.

Harris, E. N., Chan, J. K. H., Asherson R. A. Aber, V. R., Gharavi, A. E. and Hughes, E. R. V. (1986). Arch. Intern. Med. 146, 2153–2156.

Hashimoto K., Nishioka T., Tokao T., Numata Y. (1993). Endocr. J. 40:705–709.

Haskins, K. and McDuffie, M. (1 992). Science 249, 1433–1436.

Hermus A. R., Pieters G. F., Smals A. G. et al. (1988). N. Engl. J. Med. 318:1539–1560.

Hernandez E. R., Ressnick Ce., Holtzclaw W. D., Payne D. E., Adler E. Y. (1988). Endocrinol. 122:2034–2040.

Heyman, B. (1990). Immunology Today 11,310–313.

Hogan J. C. (1997) Nature Biotech. 15, 328–330.

Holte J., Bergh T., Beme C., Wide L. and Lithell H. (1995). J. Clin. Endocrinol. Metab. 80:2586–2593.

Hinek. A. (1994). Cell. Adhesion and Communication 2, 185–193.

Hoffman, R. P., Arslanian, S., Drash, A L. and Becker, D. J. (1994). J. Pediatr. Endocrinol. 7, 235–244.

Hoops, T. C., Ivanov, I., Cui, Z., Colomer-Gould, V. and Rindler, M. J. (1993). J. Biol. Chem. 268, 25694–25705.

Howell, S. L., Green. I. C. and Montague W. (1973). Biochem J. 136, 343–349.

Hrnciar J., Hrnciarova M., Jakubikova K., Okapcova J. (1992). Vntr. Lek. 38:427–437.

Kabadi V. M. and Eisenstein A. B. (1980). J. Clin. Endocrinol. Metab. 50: 392–396.

Kendall, D. M., Rooney, D. P., Smets, Y. F. C., Bolding, L. S. and Robertson, R. P. (1997). Diabetes 46, 249–257.

Kirshner M. A., Zucker I. R., Jesperson D. (1976). N. Engl. J. Med. 294:637–640.

Kleinbaum, J. and Shamoon, H. (1983). Diabetes 32, 493–498.

Laakso M, et al., (1 991) Ateriioscler. Thromb. 11: 1068–1076.

Lafer, E. M. Rauch, J., Andrezejewski Jr C., Mudd, D. Furie, B. Schwartz, R. S. and Stollar, D. 11981). J. Exp. Med. 153, 897–910.

Laine, J., Pelletier. G., Peng, M. and Le Bel, D. (1996). J. Histochem. and Cytochem., 44, 481–499.

Landowski, T. H., Dratz, E. A. and Starkey, J. R. (1995). Biochemistry 34, 11276–11287.

Landowski, T. H. and Uthayakumar, S. (1995). Clin. Exp. Metastasis 13, 357–372.

Lane, P. H., Steffes, M. W. and Mauer, S. H. (1990). Semin. Nephrol., 10, 254–259.

Leahy, J. L. (1990). Diabetes Care. 13, 992–1010.

Leibowitz G., Tsur A., Chayen S. D., Salarneh M., Raz I., Cerasi E. and Gross D. J. (1996). Clin. Endocrinol. 44:717–722.

Le Stunff C. and Bougneres P. (1994). Diabetes: 696–702.

Le Stunff C. L. and Bougneres P. F. (1996). Am. J. Physiol. 271:E814–820.

Levine, S. R. and Welch, K. M. A. (1987). Arch. Neurol. 44,876–883.

Lopez-Casillas, F., Payne, H. M., Andres, J. L. and Massague, J. (1994). J. Cell. Biol., 24, 557–568.

Love. P. E. and Santoro, S. A. (1990). Ann. Intern. Med. 112,682–698.

Ludvigsson, J. and Heding, L. (1982). Acta Diabetol Lat., 19, 351–358.

Magoffin D. A., Kurtz K. M., Erickson G. F. (1990). Mol. Endocrinol. 4:489–494.

Marchetti, P., Scharp, D. W., McLear, M., Gingerich, R., Finke, E., Olack, B., Swanson, C., Giannarelli, R., Navalesi, R. and Lacy, P. E. (1994). Diabetes, 43, 827–830.

Massia, S. P., Rao S. S. and Hubbell, J. A. (1993). J. Biol. Chem., 268, 8053–8059.

Matteucci E., Migliorini P., Bertoni C., Doicher M. P., Marchini B., Giampietro O. (1996). Clin. Rheumatol. 15: 20–24.

Mizisin, A. P., Calcutt, N. A., DiStefano, P. S., Acheson, A. and Longo, F. M. (1997). Diabetes, 46, 647–652.

Moghetti P., Castello R., Negri C., Tosi F., Spiazzi G. G., Brun E., Balducci R. Toscano V., Muggeo M. (1996). J. Clin. Endocrinol. Metab. 81:881–886.

Moghetti P., Castello R., Tosi F., Zenti M. G. M., Magnani C., Bolner A., Perobelli L. Muggeo M. (1994). J. Clin. Endocrinol. Metab. 78:169–173.

Moller D. E., Chang P. Y., Yaspelkis B. B 3rd., Flier J. S., Wallberg-Henriksson H., Ivy J. L. (1996). Endocrinology. 137:2397–2405.

Nagamani M., Hannigan E. V., Dinh T. V., Stuart, C. A. (1988). J. Clin. Endocrinol. Metab. 67:144–148.

Nijpels, G., Popp-Snijders, C., Kostense, P. J., Bouter, L. M. and Heine, R. J. (1996). Diabetologia, 39, 113–118.

Ohneda. A., Kobayashi. T., Nihei, J., Tochino, Y., Kanaya, H. and Makino, S. (1984). Diabetologia 27, 460–463.

O'Meara N. M., Blackman J. D., Sturis J., Polonsky K. S. (1993). J. Clin. Endocrinol. Metab. 76:79–84.

Payami H., Thongon G. (1989). Genet. Epidemiol. 6:137–141

Pengo, V., Thiagarajan, P., Shapiro, S. S. and Heine M. J. (1987). Blood 70,69–76.

Perez F. R., Casabiel X., Canina J. P., Zugaza J. L. Casanueva F. F. (1997). Endocrinol. 138:264–272.

Piedrola G., Novo E., Serrano-Gotarredona J., Escobar-Morreale H. F., Villa E., Luna J. D., Garcia-Robles R. (1996). J. Hypertens 14:1477–1482.

Powers, A. C., Prochazka, M., Naggert, J., Leiter, E. H. and Eisenbarth, E. S. (1993). J. Clin. Invest. 92, 359–371.

Pimenta, W., Korythowski, M., Mitrakou, A., Jenssen, T., Yki-Jarvinen, H., Evron, W., Dailey, G. and Gerich, J. (1995). JAMA 273, 1855–1861.

Pimplikar, S. W. and Huttner, W. B. (1992). J. Biol. Chem. 267,4110–4118.

Pipeleers, D. G., Schuit, F. C., in't Veld, P. A., Maes, E., Hooge-Peters, E. C., Van de Winkel, M. and Gepts, W. (1985). Endocrinology 117, 824–833.

Porksen, N. Munn, S., Steers, J., Vore, S., Veldhuis, J. and Butler, P. (1995). Am. J. Physiol. 269, E478–488.

Prentki, M. and Matschinsky, F. M. (1987). Physiol. Rev. 67, 1185–1249.

Rassmussen, H., Zawasich, K. S., Ganessan, S., Calle, R. and Zawalich, W. S. (1990). Diabetes Care 13, 655–666.

Rauch, J. Tannenbaum, H., Stoller, B. D. and Schwartz R. S. (1984). Eur. J. Immunol. 14, 529–534.

Reaven G. M. (1995). Physiol. Rev. 75:473–486.
Reaven G. M. (1988). Diabetes 37: 1595–1607.
Reinke M., Nieke J., Krestin G. P., Saeger W., Allolio B., Winkelmann W. (1992). J. Clin. Endocrinol. Metab. 75: 826–832.
Rekvig, O. P., Moens, U., Sundsfjord, A., Bredholt, G., Osei, A., Haaheim, H., Traavik, T., Amesen, E. and Haga, H.-J. (1997). J. Clin. Invest. Pp, 2045–2054.
Robinson P. and Hederer R. (I1994). Braz. J. Med. Biol. Res. 27: 263–267.
Roder, M. E., Knip, M., Hartling, S. G., Karjalainen, J., Akerblom, K., Binder, C. and the Childhood Diabetes in Finland Study Group. J. Clin. Endocrinol. Metab. (1994). 79, 1570–1575.
Roep, B. O. (1996). Diabetes 45, 1147–1156.
Roep, B. O., DeVries, R. R. P. (1992). Eur. J. Clin. Invest. 22, 697–771.
Rosen, C. L., Lisanti, M. P. and Salazer, J. L. (1992). J. Cell. Biol. 117, 617–627.
Rosenfield R. L (1996). J. Clin. Endocrinol. Metab. 81:878–880.
Roy M. S., Roy A., Gallucci W. T., Collier B., Young K., Kamilaris T. C., Chrousos G. P. (1993). Metabolism 42:696–700.
Salonen el al., (1998) Diabetes 47: 270–275.
Sammaritano, L. R., Gharavi, A. E., and Lockshin M. D. (1990). Semin. Arthritis Rheum. 20, 81–96.
Samuels M. H., Veldhuis J. D., Henry P., Ridgway E. C. (1990). J. Clin. Endocrinol. Metab. 71:432–452.
Santoro N., Filiconi M., Crowley W. F. (1986). Endocr. Rev. 7:11–23.
Schoenfeld, Y., Rauch, J., Massicotte, H., Datta. S. K. Andre-Schwartz J., Stollar, B. D. and Schwartz, R. S. (1983). N. Engl. J. Med. 308,414–420.
Schuit, F. C. and Pipeleers, D. G. (1985). Endocrinology 117, 834–840.
Serreze, D. V., Chapman, H. D., Varnum, D. S., Hanson, M. S., Reifsnyder, P. C., Richard, S. D., Fleming, S. A., Leiter, E. H. and Schultz, D. C. (1996). J. Exp. Med. 184, 2049–2053.
Sharma K., Ziyadeh, F. N. (1994). Am. J. Physiol. 267, F1094–1101.
Shaver J. K., Tezrlman S., Siperstein A. E., Duh Q. Y., Clark O. H. (1993)., Surgery 114:1064–1069.
Shenoy-Scaria, A. M., Kwong, J., Fujita, T., Olszowy, M. W., Shaw, A. S. and Lublin, D. M. (1992). J. Immunol. 149, 3535–3541.
Shimada, A., Charlton, B., Taylor-Edwards, C. and Fathman, C. G. (1996). Diabetes 45, 1063–1067.
Sibley, R., Sutherland, D. E. R., Goetz, F. and Michael, A. F. (1985). Lab. Invest. 53, 132–144.
Smeenk. R. J. J., Lucasson W. A. M. and Swaak, T. J. G. (1987). Arthritis Rheum. 30,607–617.
Sodoyez, J. L and Pipeleers, D. G. (1985). Endocrinology 117,841–848.
Sonnenberg, G. E., Hoffman, R. G., Johnson, C. P. and Kissebah, A. H. (1992). J. Clin. Invest. 90, 545–553.
Soriani, M. and Freiburghaus A. U. (1996). Int. J. Biochem. Cell. Biol. 28, 683–695.
Sowers et al (1993) Am J. Hypertens. 7:772–788.
Standl E. (1995). Clin. Invest. Med. 18:261–266.
Storch, M. J., Rossle, M. and Kerp, C. (1993). Dtsch. Med. Wochenschr. 118, 134–138.
Suzuki et al (1996) Hypertension 28: 592–598.
Talamini R., Franceschi S., Favero A., Negri E., Parazzini F., La Vecchia C. (11997). Br. J. Cancer 75:1699–1703.
Tayek J. A. (1992). J. Am. Coll. Nutr. 11:445–456.
Tayek J. A. (1995). J. Am. Coll. Nutr. 14:341–348.
Thiagarajan, P., Shapiro, S. S. and Marco, L. D. (1980). J. Clin. Invest. 66, 397–405.
Tisch, R., and McDevitt H. (1996). Cell 85: 291–297.
Towbin, H., Staeholin, T. and Gordon, J. (1979) Proc. Natl. Acad. Sci. USA 76, 4350–4354.
Tran T. T., Medline A., Bruce W. R. (1996). Cancer Epidemiol. Biomarkers Prev. 5:1013–1015.
Udenfriend, S. and Kodukula, K. (1995). Ann. Rev. Biochem. 64, 563–591.
Van Schravendijk, F. H., Forriers, A., Hoghe-Peters, E. L., Rogiers, V., De Meyts, P.,
Veinstein, A., Bordwell, B., Stone, B., Tibbetts, C. and Rothfield, N. F. (1983). Am. J. Med. 74,206–216.
Vestergaard H., Skott P., Steffensen R., Wroblewski H., Pedersen O., Kastrup J. (1995). Metabolism 44:876–882.
Villa M. C., Cozza E. N., Lima C., Ramirez M. I., De Lederkremer R. M. (1995). Cell. Signal. 73:331–339.
Wenniund A., Felig P., Hagenfeldt L., Wahren J. (1986). J. Clin. Endocrinol. Metab. 65:174–180.
Westerlund, J. Gylfe E., and Bergsten, P. (1997). J. Clin. Invest. 100:2547–2551.
Won J. G., Orth D. N. (1995). Endocrinology 136: 5399–5408.
Yamamoto, T., Nakamura, T., Noble, N. A., Ruoslahti, E. and Border, W. A. (1993). Proc. Natl. Acad. Sci. USA 90, 1814–1818.

What is claimed is:

1. An isolated antibody or fragment thereof which specifically binds to both an anti-T cell receptor (TCR) Vβ antibody and a glycosyl phosphatidyl inositol (GPI) linkage epitope.

2. The antibody or fragment thereof according to claim 1, wherein the glycosyl phosphatidyl inositol linkage epitope is a glycosyl phosphatidyl inositol linked TCR Vβ chain.

3. The antibody or fragment thereof according to claim 1, which further specifically binds to at least one member selected from the group consisting of a phospholipid, a phospholipid glycan, a single stranded DNA, and a double stranded DNA.

4. The antibody or fragment thereof according to claim 1, which further specifically binds to at least one member selected from the group consisting of a phosphatidyl inositol, phosphatidyl serine, phospholipid glycan, cardiolipin (diacyl glycerol), single stranded DNA, double stranded DNA, human pancreatic islet cell, follicular cells of the thyroid, cells of the adrenal medulla, stomach and intestinal tract, salivary glands, striated muscle, and connective tissue.

5. The antibody or fragment according to claim 1, which is a monoclonal antibody.

6. The antibody or fragment according to claim 1, which is of vertebrate or invertebrate origin.

7. The antibody or fragment according to claim 1, which is derived from B cells immortalized by Epstein-Barr virus transformation.

8. The antibody or fragment according to claim 1, which is derived from B cells obtained from healthy or diseased humans or animals.

9. The antibody or fragment according to claim 1, which is isolated by passing body fluid from an animal down an antigen conjugated column.

10. The antibody or fragment according to claim 1, further comprising an effector or reporter molecule.

11. The antibody or fragment according to claim 1, wherein the effector or reporter molecule is selected from the group consisting of an enzyme, an indicator compound, a drug, a toxin and a radioactive label.

12. The antibody or fragment according to claim 1, which is bound to a biological or synthetic substance.

13. A composition comprising the antibody or fragment according to claim 1 together with a pharmaceutically acceptable carrier.

* * * * *

SEQUENCE LISTING

<160> NUMBER OF SEQ ID NOS: 7

<210> SEQ ID NO 1
<211> LENGTH: 1231
<212> TYPE: DNA
<213> ORGANISM: Homo sapiens
<220> FEATURE:
<221> NAME/KEY: CDS
<222> LOCATION: (2)..(1231)
<223> OTHER INFORMATION:

<400> SEQUENCE: 1

```
g caa ttc cgg gat gaa cag ggc ccc atc cgc tgc aac acc aca gtc tgc     49
  Gln Phe Arg Asp Glu Gln Gly Pro Ile Arg Cys Asn Thr Thr Val Cys
   1               5                  10                  15
```

| | |
|---|---|
| ctg ggc aaa atc ggc tcc tac ctc agt gct agc acc aga cac agg gtc<br>Leu Gly Lys Ile Gly Ser Tyr Leu Ser Ala Ser Thr Arg His Arg Val<br>            20                     25                     30 | 97 |
| ctt acc tct gcc ttc agc cga gcc act agg gac ccg ttt gca ccg tcc<br>Leu Thr Ser Ala Phe Ser Arg Ala Thr Arg Asp Pro Phe Ala Pro Ser<br>            35                     40                     45 | 145 |
| cgg gtt gcg ggt gtc ctg ggc ttt gct gcc acc cac aac ctc tac tca<br>Arg Val Ala Gly Val Leu Gly Phe Ala Ala Thr His Asn Leu Tyr Ser<br>  50                         55                     60 | 193 |
| atg aac gac tgt gcc cag aag atc ctg cct gtg ctc tgc ggt ctc act<br>Met Asn Asp Cys Ala Gln Lys Ile Leu Pro Val Leu Cys Gly Leu Thr<br>65                     70                     75                   80 | 241 |
| gta gat cct gag aaa tcc gtg cga gac cag gcc ttc aag gcc att cgg<br>Val Asp Pro Glu Lys Ser Val Arg Asp Gln Ala Phe Lys Ala Ile Arg<br>                     85                     90                     95 | 289 |
| agc ttc ctg tcc aaa ttg gag tct gtg tcg gag gac ccg acc cag ctg<br>Ser Phe Leu Ser Lys Leu Glu Ser Val Ser Glu Asp Pro Thr Gln Leu<br>          100                    105                   110 | 337 |
| gag gaa gtg gag aag gat gtc cat gca gcc tcc agc cct ggc atg gga<br>Glu Glu Val Glu Lys Asp Val His Ala Ala Ser Ser Pro Gly Met Gly<br>          115                    120                   125 | 385 |
| gga gcc gca gct agc tgg gca ggc tgg gcc gtg acc ggg gtc tcc tca<br>Gly Ala Ala Ala Ser Trp Ala Gly Trp Ala Val Thr Gly Val Ser Ser<br>130                     135                    140 | 433 |
| ctc acc tcc aag ctg atc cgt tcg cac cca acc act gcc cca aca gaa<br>Leu Thr Ser Lys Leu Ile Arg Ser His Pro Thr Thr Ala Pro Thr Glu<br>145                     150                    155                  160 | 481 |
| acc aac att ccc caa aga ccc acg cct gaa gtt cct gcc cca gcc ccc<br>Thr Asn Ile Pro Gln Arg Pro Thr Pro Glu Val Pro Ala Pro Ala Pro<br>          165                    170                   175 | 529 |
| acc cct gtt cct gcc acc cct aca acc tca ggc cac tgg gag acg cag<br>Thr Pro Val Pro Ala Thr Pro Thr Thr Ser Gly His Trp Glu Thr Gln<br>          180                    185                   190 | 577 |
| gag gag gac aag gac aca gca gaa gac agc agc act gct gac aga tgg<br>Glu Glu Asp Lys Asp Thr Ala Glu Asp Ser Ser Thr Ala Asp Arg Trp<br>          195                    200                   205 | 625 |
| gac gac gaa gac tgg ggc agc ctg gag cag gag gcc gag tct gtg ctg<br>Asp Asp Glu Asp Trp Gly Ser Leu Glu Gln Glu Ala Glu Ser Val Leu<br>210                     215                    220 | 673 |
| gcc cag cag gac gac tgg agc acc ggg ggc caa gtg agc cgt gct agt<br>Ala Gln Gln Asp Asp Trp Ser Thr Gly Gly Gln Val Ser Arg Ala Ser<br>225                     230                    235                  240 | 721 |
| cag gtc agc aac tcc gac cac aaa tcc tcc aaa tcc cca gag tcc gac<br>Gln Val Ser Asn Ser Asp His Lys Ser Ser Lys Ser Pro Glu Ser Asp<br>          245                    250                   255 | 769 |
| ttg gag caa ctg gga agc tta agg gtc ctt gga aca cgg ctg gcc agc<br>Leu Glu Gln Leu Gly Ser Leu Arg Val Leu Gly Thr Arg Leu Ala Ser<br>          260                    265                   270 | 817 |
| gag tat aac tgg ggt tgc cca gag tcc agc gac aag ggc gac ccc ttc<br>Glu Tyr Asn Trp Gly Cys Pro Glu Ser Ser Asp Lys Gly Asp Pro Phe<br>          275                    280                   285 | 865 |
| gct acc ctg tct gca cgt tcc agc acc cag ccg agg cca gac tct tgg<br>Ala Thr Leu Ser Ala Arg Ser Ser Thr Gln Pro Arg Pro Asp Ser Trp<br>290                     295                    300 | 913 |
| ggt gag gac aac tgg gag ggc ctc gag act gac agt cga cag gtc aag<br>Gly Glu Asp Asn Trp Glu Gly Leu Glu Thr Asp Ser Arg Gln Val Lys<br>305                     310                    315                  320 | 961 |
| gct gag ctg gcc cgg aag aag cgc gag gag cgg cgg cgg gag atg gag<br>Ala Glu Leu Ala Arg Lys Lys Arg Glu Glu Arg Arg Arg Glu Met Glu | 1009 |

```
                       325                 330                 335
gcc aaa cgc gcc gag agg aag gtg gcc aag ggc ccc atg aag ctg gga      1057
Ala Lys Arg Ala Glu Arg Lys Val Ala Lys Gly Pro Met Lys Leu Gly
        340                 345                 350 gcc cgg aag ctg gat gaa ccg tgg cgg tgg ccc ttc ccg gct gcg gag      1105
Ala Arg Lys Leu Asp Glu Pro Trp Arg Trp Pro Phe Pro Ala Ala Glu
        355                 360                 365 agc ccg ccc cac aga tgt att tat tgt aca aac cat gtg agg ccg gcc      1153
Ser Pro Pro His Arg Cys Ile Tyr Cys Thr Asn His Val Arg Pro Ala
        370                 375                 380 ggc cca gcc agg cca ttc acg tgt aca taa tca gag cca caa taa att      1201
Gly Pro Ala Arg Pro Phe Thr Cys Thr     Ser Glu Pro Gln     Ile
385                 390                         395 tta ttt cac aaa aaa aaa acc gga atg gcc                              1231
Leu Phe His Lys Lys Lys Thr Gly Met Ala
        400                 405

<210> SEQ ID NO 2
<211> LENGTH: 393
<212> TYPE: PRT
<213> ORGANISM: Homo sapiens
<220> FEATURE:
<223> OTHER INFORMATION: Novel Sequence

<400> SEQUENCE: 2

Gln Phe Arg Asp Glu Gln Gly Pro Ile Arg Cys Asn Thr Thr Val Cys
1               5                   10                  15

Leu Gly Lys Ile Gly Ser Tyr Leu Ser Ala Thr Arg His Arg Val
                20                  25                  30

Leu Thr Ser Ala Phe Ser Arg Ala Thr Arg Asp Pro Phe Ala Pro Ser
            35                  40                  45

Arg Val Ala Gly Val Leu Gly Phe Ala Ala Thr His Asn Leu Tyr Ser
        50                  55                  60

Met Asn Asp Cys Ala Gln Lys Ile Leu Pro Val Leu Cys Gly Leu Thr
65                  70                  75                  80

Val Asp Pro Glu Lys Ser Val Arg Asp Gln Ala Phe Lys Ala Ile Arg
                85                  90                  95

Ser Phe Leu Ser Lys Leu Glu Ser Val Ser Glu Asp Pro Thr Gln Leu
            100                 105                 110

Glu Glu Val Glu Lys Asp Val His Ala Ala Ser Ser Pro Gly Met Gly
        115                 120                 125

Gly Ala Ala Ser Trp Ala Gly Trp Ala Val Thr Gly Val Ser Ser
        130                 135                 140

Leu Thr Ser Lys Leu Ile Arg Ser His Pro Thr Thr Ala Pro Thr Glu
145                 150                 155                 160

Thr Asn Ile Pro Gln Arg Pro Thr Pro Glu Val Pro Ala Pro Ala Pro
                165                 170                 175

Thr Pro Val Pro Ala Thr Pro Thr Thr Ser Gly His Trp Glu Thr Gln
            180                 185                 190

Glu Glu Asp Lys Asp Thr Ala Glu Ser Ser Thr Ala Asp Arg Trp
        195                 200                 205

Asp Asp Glu Asp Trp Gly Ser Leu Glu Gln Glu Ala Glu Ser Val Leu
        210                 215                 220

Ala Gln Gln Asp Asp Trp Ser Thr Gly Gly Gln Val Ser Arg Ala Ser
225                 230                 235                 240

Gln Val Ser Asn Ser Asp His Lys Ser Ser Lys Ser Pro Glu Ser Asp
                245                 250                 255
```

```
Leu Glu Gln Leu Gly Ser Leu Arg Val Leu Gly Thr Arg Leu Ala Ser
        260                 265                 270

Glu Tyr Asn Trp Gly Cys Pro Glu Ser Ser Asp Lys Gly Asp Pro Phe
    275                 280                 285

Ala Thr Leu Ser Ala Arg Ser Ser Thr Gln Pro Arg Pro Asp Ser Trp
    290                 295                 300

Gly Glu Asp Asn Trp Glu Gly Leu Glu Thr Asp Ser Arg Gln Val Lys
305                 310                 315                 320

Ala Glu Leu Ala Arg Lys Lys Arg Glu Glu Arg Arg Glu Met Glu
                325                 330                 335

Ala Lys Arg Ala Glu Arg Lys Val Ala Lys Gly Pro Met Lys Leu Gly
            340                 345                 350

Ala Arg Lys Leu Asp Glu Pro Trp Arg Trp Pro Phe Pro Ala Ala Glu
            355                 360                 365

Ser Pro Pro His Arg Cys Ile Tyr Cys Thr Asn His Val Arg Pro Ala
    370                 375                 380

Gly Pro Ala Arg Pro Phe Thr Cys Thr
385                 390

<210> SEQ ID NO 3
<211> LENGTH: 4
<212> TYPE: PRT
<213> ORGANISM: Homo sapiens
<220> FEATURE:
<223> OTHER INFORMATION: Novel Sequence

<400> SEQUENCE: 3

Ser Glu Pro Gln
1

<210> SEQ ID NO 4
<211> LENGTH: 11
<212> TYPE: PRT
<213> ORGANISM: Homo sapiens
<220> FEATURE:
<223> OTHER INFORMATION: Novel Sequence

<400> SEQUENCE: 4

Ile Leu Phe His Lys Lys Lys Thr Gly Met Ala
1               5                   10

<210> SEQ ID NO 5
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 5
gtagacccaa gctttcctgg agcatgtcag tataggagg                              39

<210> SEQ ID NO 6
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 6
ctgctcgagc ggccgcatgc tagcgaccgg cgctcagctg g                           41
```

```
-continued

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Val Gly Val Ala Pro Gly
1               5
```